(12) United States Patent
Thabet, II et al.

(10) Patent No.: US 11,197,760 B2
(45) Date of Patent: Dec. 14, 2021

(54) SYSTEM AND METHOD TO FUSE BONE

(71) Applicant: CryoHeart Laboratories, Inc., Highlands Ranch, CO (US)

(72) Inventors: Frederick J. Thabet, II, Highlands Ranch, CO (US); Ravi Kanagala, Highlands Ranch, CO (US); James Searle, Highlands Ranch, CO (US)

(73) Assignee: Cryoheart Laboratories, Inc., Boca Raton, FL (US)

( * ) Notice: Subject to any disclaimer, the term of this patent is extended or adjusted under 35 U.S.C. 154(b) by 102 days.

(21) Appl. No.: 16/517,276

(22) Filed: Jul. 19, 2019

(65) Prior Publication Data

US 2020/0022814 A1 Jan. 23, 2020

Related U.S. Application Data

(60) Provisional application No. 62/700,378, filed on Jul. 19, 2018.

(51) Int. Cl.
*A61F 2/28* (2006.01)
*A61F 2/30* (2006.01)

(52) U.S. Cl.
CPC ............ *A61F 2/28* (2013.01); *A61F 2/30749* (2013.01); *A61F 2/30771* (2013.01); *A61F 2002/2817* (2013.01); *A61F 2002/3092* (2013.01); *A61F 2002/3093* (2013.01); *A61F 2002/30576* (2013.01); *A61F 2002/30677* (2013.01); *A61F 2002/30784* (2013.01); *A61F 2002/30884* (2013.01); *A61F 2002/30891* (2013.01); *A61F 2310/00017* (2013.01); *A61F 2310/00023* (2013.01); *A61F 2310/00359* (2013.01); *A61F 2310/00371* (2013.01)

(58) Field of Classification Search
CPC .................. A61F 2/28; A61F 2/30749; A61F 2002/2817; A61F 2002/30576; A61F 2002/3092; A61F 2002/3093; A61B 17/68; A61B 17/8076; A61B 17/823; A61L 27/3608
See application file for complete search history.

(56) References Cited

U.S. PATENT DOCUMENTS

| | | | |
|---|---|---|---|
| 5,380,328 A | 1/1995 | Morgan | |
| 6,863,694 B1* | 3/2005 | Boyce | A61L 27/3683 623/23.63 |
| 9,585,764 B2 | 3/2017 | McKay | |
| 9,861,724 B2* | 1/2018 | Schumacher | A61L 27/10 |
| 9,987,138 B2 | 6/2018 | McKay | |
| 2015/0012107 A1* | 1/2015 | Koford | A61L 27/3608 623/23.5 |
| 2015/0245916 A1 | 9/2015 | Burkinshaw | |

OTHER PUBLICATIONS

International Search Report and Written Opinion regarding PCT/US2019/042666 dated Dec. 4, 2019.

\* cited by examiner

*Primary Examiner* — Brian A Dukert
(74) *Attorney, Agent, or Firm* — Polsinelli PC; Adam C. Rehm

(57) ABSTRACT

An implant is provided that is operable to be disposed between and fuse two sections of a bone. The implant includes an inner layer and an outer layer. The outer layer at least partially surrounds the inner layer and is operable to abut against the two sections of the bone. The outer layer is porous and/or fibrous and is operable to receive at least one cellular growth factor.

20 Claims, 18 Drawing Sheets

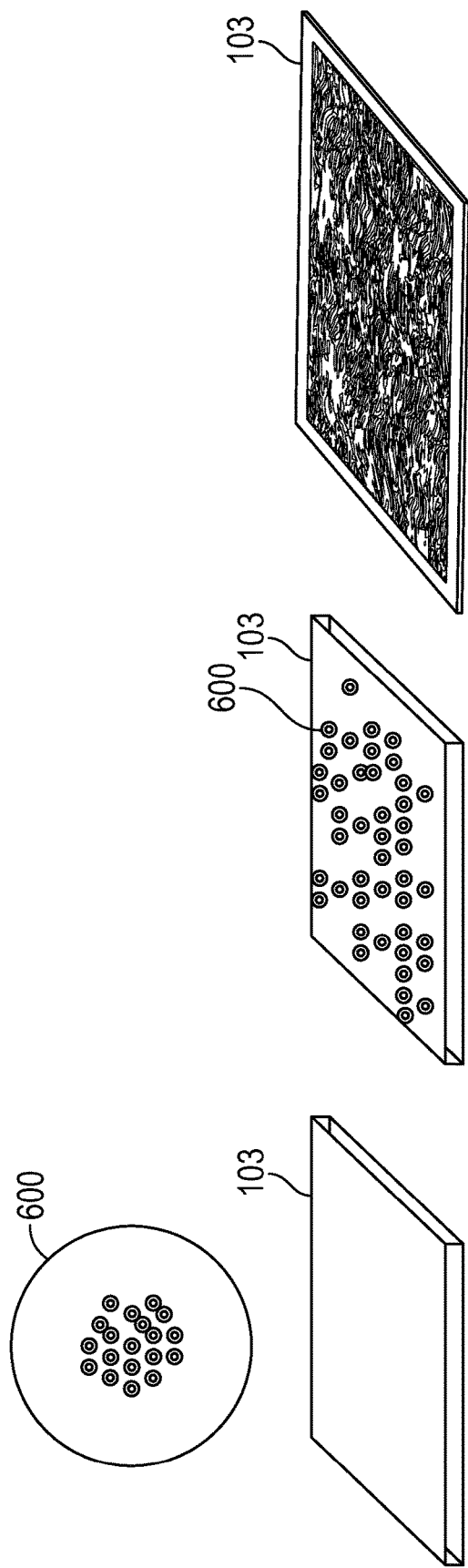

SYSTEM AND METHOD TO FUSE BONE

CROSS-REFERENCE TO RELATED APPLICATION

This application claims the benefit of U.S. Provisional Patent Application No. 62/700,378, filed in the U.S. Patent and Trademark Office on Jul. 19, 2018, which is incorporated herein by reference in its entirety for all purposes.

BACKGROUND

1. Field of the Invention

The present inventive concept relates to systems and methods to heal and/or replace bone. In at least one example, the present inventive concept relates to an implant system and method to stabilize and fuse two halves of a sternum in a patient post-sternotomy.

2. Description of Related Art

Physical intervention in tissue of a human or an animal, for example surgery, dates to prehistoric times. During a surgical procedure, an incision is made to access the interior of the body and when the procedure is complete, the incision is closed to the external environment. Some parts of the body are not directly accessible via a simple incision and present additional challenges. For example, organs such as the heart and lungs are protected within the ribcage/thoracic cage. Thus, to access a patient's heart, a surgeon often needs to separate the sternum.

The sternum or breastbone is a long, flat bone forming the middle portion of the front of the chest. Individual rib bones are connected along the sides of the sternum via cartilage to form the ribcage/thoracic cage which protects the heart, lungs, and major blood vessels from injury. The sternum is cut open in a sternotomy to gain access to the thoracic contents when performing cardiothoracic surgery.

A sternotomy is a surgical procedure in which a midline longitudinal incision is made through at least a portion of the sternum to allow opposing halves/portions to be laterally separated to provide access to organs within the ribcage/thoracic cage. When the surgical procedure is complete, the separated halves/portions are aligned with and secured to one another and the incision closed. A variety of devices, compositions, and methods for assisting with closing and healing of sternotomy wounds can be utilized.

The ideal goal for assisting with closing and healing of sternotomy wounds is complete rejoining of sternal portions with new bone growth in the absence of complications. Unfortunately, patient recovery from a conventional sternotomy is often slow and problematic. As the two sections (of the sternum) are brought back together by the surgeon, proper compression and a tight realignment of the end plates of the sternal surfaces is rarely achieved resulting in non-union, i.e. dehiscence, of separated sternal halves. This non-union allows for motion such as sliding of the surface of one sternal half against the surface of the other sternal half leading to significant pain for the patient and increased chance for development of infection. Additionally, the lack of proper compression leads to the formation of fibrous scar tissue instead of the desired new bone. If further surgical procedures are required, the scar tissue will have to be removed further complicating the procedure.

Accordingly, there is a need for an improved system and method to reduce or eliminate the above-described shortcomings which will move one closer to the goal of a sternum completely healed by new bone growth.

SUMMARY

The present inventive concept provides a system and method to fuse bone which has been separated or fractured into two sections. An implant is provided to be disposed between the two sections of the bone. The implant includes an inner layer including a cortical bone graft and an outer layer at least partially surrounding the inner layer. The implant is sized and shaped such that substantially all of the split surfaces of the two sections are compressed against the implant. Accordingly, the implant can accelerate and promote fusion of the bone.

The aforementioned may be achieved in an aspect of the present inventive concept by providing an implant operable to be disposed between and fuse two sections of a bone. The implant may include an inner layer and an outer layer. The outer layer may at least partially surround the inner layer and may be operable to abut against the two sections of the bone. The outer layer may be porous and/or fibrous and may be operable to receive at least one cellular growth factor.

The outer layer may include a first portion and a second portion. The inner layer may be sandwiched between the first and second portions of the outer layer. The outer layer may be wrapped around a circumference of the inner layer.

The inner layer and/or the outer layer may include tissue, for example bone tissue. The inner layer and/or the outer layer may include at least a portion of at least one of the following: cortical bone fibers, cancellous bone fibers, collagen sponge, cortical bone graft, synthetic bone, and/or tissue graft. The at least one cellular bone growth factor may include bone morphogenetic proteins, mesenchymal stem cells, blood, osteoclasts, osteoblasts, antibiotics, analgesics, and/or medications. The inner layer may be fenestrated to promote bone growth.

The implant may have a thickness between about 2 millimeters and about 100 millimeters, alternately between about 2 millimeters and about 50 millimeters, alternately between about 2 millimeters and about 25 millimeters. The implant may have a length between about 25 millimeters and about 250 millimeters, alternately between about 25 millimeters and about 150 millimeters, alternately between about 25 millimeters and about 75 millimeters. The implant may have a depth between about 1 millimeters and about 30 millimeters, alternately between about 1 millimeters and about 20 millimeters, alternately between about 1 millimeters and about 10 millimeters.

One or more tacks may extend from at least one of the inner layer or the outer layer and may be operable to couple with the bone. The one or more tacks may include bone tissue, vicryl, polypropylene, stainless steel, titanium, polyether ether ketone (PEEK), polyetherketone (PEK), polymers, metals, and/or poly(methyl methacrylate) (PMMA).

The inner layer may include two tabs which extend from each end of the outer layer. The tabs may be operable to provide compression and stability to assist in anchoring the implant between the two sections of the bone.

Also, the aforementioned may be achieved in an aspect of the present inventive concept by providing a method to fuse two sections of a bone. The method may include disposing an implant between the two sections of the bone. The implant may include an inner layer and an outer layer. The outer layer may at least partially surround the inner layer and may be operable to abut against the two sections of the bone.

The outer layer may be porous and/or fibrous and may be operable to receive at least one cellular growth factor. The implant may be compressed between the two sections of the bone such that the outer layer is abutting against the two sections of the bone. The compression of the implant and the two sections of the bone may be secured so that one or more loads are created. The one or more loads may be one or more forces acting on, e.g., opposing, at least one side of the two sections of the bone or each of the two sections of the bone. The one or more loads may be equally or unequally exerted on each of the two sections of the bone. The compression of the implant and/or the two sections of the bone may be secured using one or more securing elements, e.g., one or more fasteners such as a wire. The one or more securing elements may provide or at least supplement the one or more loads acting on or opposing both of the two sections of the bone. In this manner, the one or more securing elements may be one or more load-creating elements.

The inner layer and/or the outer layer may include tissue, for example bone tissue. The inner layer and/or the outer layer may include at least a portion of at least one of the following: cortical bone fibers, cancellous bone fibers, collagen sponge, cortical bone graft, synthetic bone, and/or tissue graft. The method may further include soaking the implant in the at least one cellular growth factor. The at least one cellular bone growth factor may include bone morphogenetic proteins, mesenchymal stem cells, blood, osteoclasts, osteoblasts, antibiotics, analgesics, and/or medications. The inner layer may be fenestrated to promote bone growth.

The implant may have a thickness between about 2 millimeters and about 100 millimeters, alternately between about 2 millimeters and about 50 millimeters, alternately between about 2 millimeters and about 25 millimeters. The implant may have a length between about 25 millimeters and about 250 millimeters, alternately between about 25 millimeters and about 150 millimeters, alternately between about 25 millimeters and about 75 millimeters. The implant may have a depth between about 1 millimeters and about 30 millimeters, alternately between about 1 millimeters and about 20 millimeters, alternately between about 1 millimeters and about 10 millimeters. The method may include cutting the implant to a predetermined thickness, length, and/or depth.

The implant may be coupled with the bone by inserting one or more tacks extending from at least one of the inner layer or the outer layer into the bone. The one or more tacks may include bone tissue, vicryl, polypropylene, stainless steel, titanium, polyether ether ketone (PEEK), polyetherketone (PEK), polymers, metals, and/or poly(methyl methacrylate) (PMMA).

The foregoing is intended to be illustrative and is not meant in a limiting sense. Many features of the embodiments may be employed with or without reference to other features of any of the embodiments. Additional aspects, advantages, and/or utilities of the present inventive concept will be set forth in part in the description that follows and, in part, will be apparent from the description, or may be learned by practice of the present inventive concept.

BRIEF DESCRIPTION OF THE DRAWINGS

The foregoing summary, as well as the following detailed description, will be better understood when read in conjunction with the appended drawings. For the purpose of illustration, there is shown in the drawings certain embodiments of the present disclosure. It should be understood, however, that the present inventive concept is not limited to the precise embodiments and features shown. The accompanying drawings, which are incorporated in and constitute a part of this specification, illustrate an implementation of apparatuses consistent with the present inventive concept and, together with the description, serve to explain advantages and principles consistent with the present inventive concept.

FIGS. 24A-C are diagrams illustrating a surface treatment for an implant; and

FIG. 25 is a flow chart of a method for utilizing an implant.

DETAILED DESCRIPTION

Figure 1:
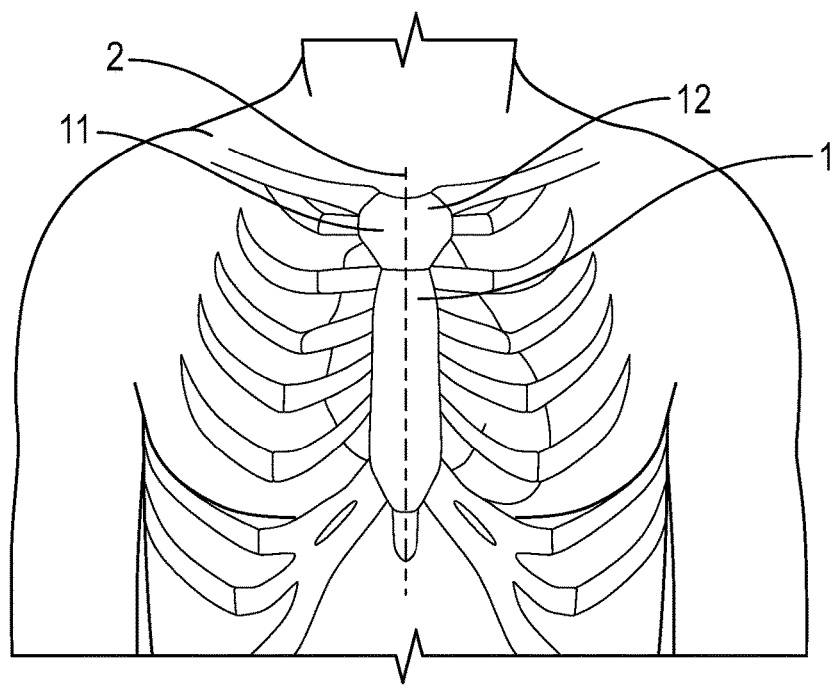
FIG. 1 is a diagram illustrating a sternum with a separation site.

The following detailed description references the accompanying drawing that illustrates various embodiments of the present inventive concept. The illustration and description are intended to describe aspects and embodiments of the present inventive concept in sufficient detail to enable those skilled in the art to practice the present inventive concept. Other components can be utilized and changes can be made without deviating from the scope of the present inventive concept. The following detailed description is, therefore, not to be taken in a limiting sense. The scope of the present inventive concept is defined only by the appended claims, along with the full scope of equivalents to which such claims are entitled.

I. Terminology

The phraseology and terminology employed herein are for the purpose of description and should not be regarded as limiting. For example, the use of a singular term, such as, "a" is not intended as limiting of the number of items. Also, the use of relational terms such as, but not limited to, "top," "bottom," "left," "right," "upper," "lower," "down," "up," and "side," are used in the description for clarity in specific reference to the figures and are not intended to limit the scope of the present inventive concept or the appended claims. The term "automatic," "automatically," or any variation thereof is used in the description to describe performing a subsequent action without any assistance, interference, and/or input from a human. Further, it should be understood that any one of the features of the present inventive concept may be used separately or in combination with other features. Other systems, methods, features, and advantages of the present inventive concept will be, or become, apparent to one with skill in the art upon examination of the figures and the detailed description. It is intended that all such additional systems, methods, features, and advantages be included within this description, be within the scope of the present inventive concept, and be protected by the accompanying claims.

The term "implant" or "surgical implant" can refer to a medical device manufactured to replace a missing biological structure, support a damaged biological structure, or enhance an existing biological structure.

The term "bone grafting," "bone graft," or any variation thereof can refer to any surgical procedure for replacing missing bone and/or adding new bone. In some examples, bone grafts can replace lost bone with new bone and/or bone tissue. In some examples, bone grafts can promote healing, reduced pain, increased spirometer readings, improved sternal alignment and/or reduced dehiscence risks related to the stabilization, alignment, and/or fusion of two halves of a patient's sternum which have been separated and/or fractured, for example by sternotomy. The bone graft can be an autograft obtained from the patient receiving the graft; an allograft obtained from a different individual of the same species as the patient receiving the graft; a xenograft obtained from an individual of a different species as the patient receiving the graft; and/or any synthetic bone grafts made of manufactured materials and/or imitation bone.

The term "sternotomy" can refer to the surgical procedure of cutting a patient's sternum and separating cut portions to access thoracic organs such as the heart, lungs, and/or blood vessels. While the disclosed subject matter is focused on the sternum, it is foreseen that the system and method can be utilized in relation to any separated portions of any bone.

The term "patient" can include any human being or animal. The term "subject" may also be used herein to refer to the patient.

Cortical bone or compact bone can be a dense outer surface of bone that forms a protective layer around the internal cavity of a bone. Cortical bone assists in providing body structure and weight bearing.

Cancellous bone can be a meshwork of spongy tissue of mature bone, for example found at the core of vertebral bones in the spine and/or at the ends of long bones such as the femur.

The term "bone growth-promoting material" can include any material that promotes and/or enhances bone growth. The term "bone growth-promoting agent" can include any composition or material that promotes and/or enhances bone growth. The bone growth-promoting agent added to the implant can be any known bone-growth promoting agent, including, but not limited to hydroxyapatite (HA), cellular growth factors, cytokines, and bone morphogenetic proteins (BMP). In some examples, strips of bone growth-promoting material, for example cancellous bone and/or collagen sponge, include one or more types of living cells. The living cells added to the implant can be any living cells that promote and/or enhance bone growth including, but not limited to, stem cells, osteoblasts, osteoconductive cells, osteoinductive cells, and/or osteogenic cells. In some examples, strips of bone growth-promoting material, for example cancellous bone and/or collagen sponge, can include both bone growth-promoting agents and living cells as described herein.

The term "collagen sponge" can include any known collagen-containing material or sponge.

The term "synthetic" material can include any man-made material. The synthetic material can be made from a combination of natural material and/or man-made or fabricated material. The synthetic material may not be found in nature.

Further, any term of degree such as, but not limited to, "substantially," as used in the description and the appended claims, should be understood to include an exact, or a similar, but not exact configuration. For example, "a substantially planar surface" means having an exact planar surface or a similar, but not exact planar surface. Similarly, the terms "about" or "approximately," as used in the description and the appended claims, should be understood to include the recited values or a value that is three times greater or one third of the recited values. For example, about 1 mm includes all values from 0.1 mm to 9 mm. Additionally, the term "about" can refer to near or close to the desired dimension, for example "about" can refer to near or close to disclosed thicknesses and encompassed thicknesses that can be effectively implanted into the patient.

Further, as the present inventive concept is susceptible to embodiments of many different forms, it is intended that the present disclosure be considered as an example of the principles of the present inventive concept and not intended to limit the present inventive concept to the specific embodiments shown and described. Any one of the features of the present inventive concept may be used separately or in combination with any other feature. References to the terms "embodiment," "embodiments," and/or the like in the description mean that the feature and/or features being referred to are included in, at least, one aspect of the description. Separate references to the terms "embodiment," "embodiments," and/or the like in the description do not necessarily refer to the same embodiment and are also not mutually exclusive unless so stated and/or except as will be readily apparent to those skilled in the art from the description. For example, a feature, structure, process, step, action, or the like described in one embodiment may also be included in other embodiments, but is not necessarily included. Thus, the present inventive concept may include a variety of combinations and/or integrations of the embodiments described herein. Additionally, all aspects of the present disclosure, as described herein, are not essential for its practice. Likewise, other systems, methods, features, and advantages of the present inventive concept will be, or become, apparent to one with skill in the art upon examination of the figures and the description. It is intended that all such additional systems, methods, features, and advantages be included within this description, be within the scope of the present inventive concept, and be encompassed by the claims.

The term "coupled" is defined as connected, whether directly or indirectly through intervening components, and is not necessarily limited to physical connections. The connection can be such that the objects are permanently connected or releasably connected. The terms "comprising," "including" and "having" are used interchangeably in this disclosure. The terms "comprising," "including" and "having" mean to include, but not necessarily be limited to the things so described.

Lastly, the terms "or" and "and/or," as used herein, are to be interpreted as inclusive or meaning any one or any combination. Therefore, "A, B or C" or "A, B and/or C" mean any of the following: "A," "B" or "C"; "A and B"; "A and C"; "B and C"; "A, B and C." An exception to this definition will occur only when a combination of elements, functions, steps or acts are in some way inherently mutually exclusive.

II. General Architecture

An implant to fuse bone can be utilized, for example, at the sternum after a sternotomy to access the heart. In some examples, the implant can be utilized for other bones such as ribs. For example, if a surgeon accesses the thoracic cavity by going through one or more ribs or the inner costal space, the implant can be utilized to repair the rib(s). The implant is compressed between two sections of the bone to promote bone growth and healing. Accordingly, after inserting the implant between the two sections of the bone, a load can be created to cause compression.

In at least one example, a leading edge of the implant may be exposed to the vessels and heart of the thoracic cavity. The implant can be combined with an anti-adhesion membrane on the leading edge of the implant to reduce or prevent debris from the implant from falling into the thoracic cavity as well as to help reduce or prevent scar tissue from forming at that point. Accordingly, by combining the implant with the anti-adhesion membrane, the combined tissue can act as a protective coating.

In at least one example, the implant can act as a carrier of other components. The other components can be added to the implant either prior to implantation and/or after implantation. For example, the other components can include, but are not limited to, plasma rich protein (PRP), bone marrow aspirate (BMA), saline, antibiotics, analgesics, anticoagulants, bone growth factors such as bone morphogenetic proteins (BMPs), hydroxyapatite, hyaluronic acids, beta-tricalcium phosphate (BTCP), surgical glues utilizing natural materials as well as human and/or animal tissues, demineralized bone matrix (DBM) powders, particulates, pastes, putties, cancellous chips, allograft tissues, xenograft tissues, collagen fibers, collagen matrix, and/or collagen membranes.

In at least one example, synthetic materials can be included with the implant. The synthetic materials can include, for example, titanium, stainless steel, PEEK, PEKK, surgical grade plastics of any kind, polyethylene, polymethylmethacrylate, vicryl surgical glues, synthetic surgical glues, porcelain, ceramics, and/or BioGlass. Other suitable synthetic materials which are bio-compatible can also be included without deviating from the scope of the invention. In some examples, bone materials and synthetic materials can be combined as desired.

The implant can be packaged in any suitable packaging without deviating from the scope of the invention. For example, the implant can be packaged in a double peel pack that allows for sterile and protected storage of the implant. In at least one example, the packaging can allow for sterile and protected rehydration of the implant. The implant can be rehydrated, for example, with PRP, BMA, saline, blood draw, antibiotics, analgesics, blood clotting agents, DBM liquids, DBM powders, BMPs, any synthetic material, any manmade material, and/or any combination of the above.

For implantation, the bone wound, such as a sternal wound, is measured. The implant can be rehydrated and trimmed to size according to the sternal measurements. The implant can be applied to the sternal edge, for example by using forceps. In at least one example, one or more vicryl stitches or tacks can be used to anchor the graft to the edge of the sternum. Other suitable fasteners or anchors can be utilized, for example, vicryl tack; vicryl suture; human and/or animal suture material; synthetic suture material; bone tack, plug, and/or anchor; stainless steel tack, plug, and/or anchor; titanium tack, plug, and/or anchor; any other manmade or synthetic material that is used as a tack, suture, plug, and/or anchor; any natural material, human tissue, and/or animal tissue that can be made into a tack, suture, plug, and/or anchor; DBM paste and/or putty; hydroxyapatite paste and/or putty; any suitable type of bone glue and/or bone putty; any synthetic substance that can be used with bone and/or for bone healing that can cause the implant to stick, adhere, and/or fit onto and/or into the edge of the bone; and/or TCP paste and/or putty.

In at least one example, the implant can be press fit into the bone edge via a natural void due to bone loss and/or poor bone quality. In some examples, a void can be surgically created in the bone edge. In at least one example, the implant can be secured to the bone edge with any suitable type of surgical polymer such as polymethylmethacrylate, any other suitable manmade adhesive substance, and/or any altered or non-altered human and/or animal tissue. In at least one example, the implant can be secured to the edges of the bone by utilizing wires or any other suitable closing mechanism to either support the implant, pass through the implant, wrap the implant, suspend the implant, and/or by any other suitable closing technology that impacts the implant placement into a position where the implant can aid in the healing and fusion of the bone. In at least one example, the implant can be secured to the edge of the bone with the patient's own tissue, which can be altered or non-altered. The implant can be applied to the edge of the bone by any suitable artificial or natural method that causes the implant to be held in place as the bone is being closed without deviating from the scope of the invention.

In at least one example, peptide bone glue can be included to create a load. The peptide bone glue can be utilized with or without other load-creating elements, such as those discussed herein. The adhesive nature of the peptide bone glue can facilitate bone growth.

The implant can be disposed in different locations in relation to the bone wound. While the sternum is discussed in the below examples, the implant can be disposed in different locations depending on the bone and/or the wound. For example, the implant can be placed along the inside edges of the sternal bone where the sternal bone has been incised, cut, sawed in two, or separated. In some examples, the implant can be measured and fit to be placed and run the length of the entire sternum, for example from the jugular (suprasternal) notch of the manubrium to the distal tip of the xiphoid process. In some examples, the implant can be measured and fit into place along the inside edges of the manubrium only. In some examples, the implant can be measured and fit into place along the inside edges of the manubrium, through the manubriosternal joint or second costal notch and into the body of the sternum only. In some examples, the implant can be measured and fit into place along the inside edges of the manubrium, through the manubriosternal joint or second costal notch and into the body of the sternum, including the third, fourth, fifth, and sixth costal notches of the sternum to the distal tip of the sternal body only and on through the seventh costal notch and through the body of the xiphoid process or to the distal tip of the xiphoid process. In some examples, the implant can be placed along the inside cut sternal edges of the sternal wound, and also be oriented in a mesh pattern to wrap the sternal edges with the bone mesh.

To prepare the sternal edge, if the sternal edge is bleeding aggressively prior to implantation, the surgeon may choose to use a hemostatic agent along the edge of the incised sternum to help control bleeding. By adding the implant, the surgeon can help occlude blood flow further. Prior to implantation, the sides of the incised sternal edges can be roughened to help grip the implant after implantation. For example, the sides of the incised sternal edges can be prepared with sand paper. In at least one example, having an oversized implant made of bone fibers allows the sternal edges to imbed into the implant. By embedding the sternal edges into the implant, the implant acts like a gasket and accomplishes at least one of the following benefits: hemostasis, pain relief, realignment, set the bone to fuse and heal versus stabilizing via soft tissue or scar tissue formation, stabilize the entire sternal construct, eliminate gapping and loosening of the sternal construct with wires. By reducing or eliminating the gaps that may form, the areas where bacteria can form and create infection are reduced or eliminated. After implantation of the implant, the security of the implant can be checked, for example by palpating the entire sternal structure. In some examples, antibiotics can be added or dripped onto the implant and sternal construct. In some examples, the operative site can be injected with pain medications to significantly reduce the pain levels post operatively.

In at least one example, co-morbidities may qualify as inclusion criteria to use the implant. For example, the co-morbidities can include at least one of the following: osteoporosis, diabetes, obesity, smoking, and/or vascular disease. Osteoporosis indicates poor bone quality. With diabetes, the body's ability to produce or respond to the hormone insulin is impaired. Obesity is the medical condition in which excess body fat has accumulated to an extent that produces negative effects on the body. Smoking leaches calcium from the skeletal system and decreases bone density. Smoking can also have a negative effect on bone healing. Patients undergoing cardiothoracic surgery typically experience a significant decrease in the overall quality of their health, including vascular disease. Poor overall health decreases the viability of a patient prior to surgery and makes the patient less likely to heal adequately from a large sternal wound incision. Grafting using the implant can significantly increase the patient's ability to heal appropriately post operatively.

FIG. 1 is a schematic drawing showing the interior of a human chest. The bone 1 may be separated at separation site 2. As illustrated in FIG. 1, the bone 1 is a sternum. While the disclosure focuses on the bone 1 being a sternum, in some examples, the bone 1 can be any bone that has been separated into two sections that calls for fusion. Separation site 2 may be an incision site 2, for example for a sternotomy. In some examples, the separation site 2 may be the location where the bone has been fractured or separated into two sections. As illustrated in FIG. 1, separation site 2 can provide a midline, longitudinal cut through at least part of the sternum 1 such that opposing halves separate. While separation site 2 is illustrated as a straight line, in other examples, separation site 2 can be any line, such as zig-zagged, diagonal, and/or irregular line without deviating from the scope of the disclosed inventive concept.

Figures 2A, 2B:
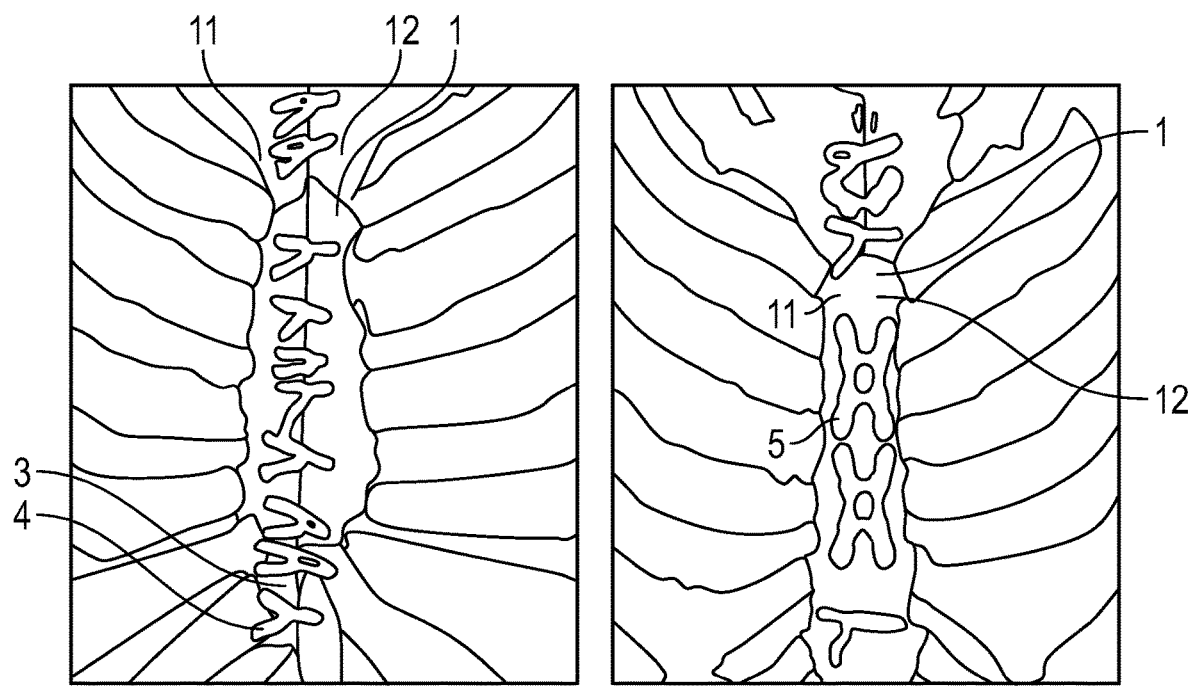
FIG. 2A is a diagram of sternal dehiscence post-surgery in which the two sections of the sternum are secured with wire fasteners.
FIG. 2B is a diagram illustrating the two sections of the sternum secured with plates and screws.

Conventionally, patient recovery from a sternotomy can be often problematic due to non-union (for example malalignment, pain, dehiscence) of separated sections 11, 12 of the sternum 1; onset of infection; and/or impaired pulmonary function. Lack of proper preparation of the sternum for closure can be a factor contributing to sternal dehiscence post-surgery. As the two sections 11, 12 of the sternum 1 are brought back together, proper compression and a tight realignment of the end plates of the two sections 11, 12 of the sternum 1 is rarely achieved. Spaces and gaps remain and/or easily reopen between two sections 11, 12. FIGS. 2A and 2B illustrate exemplary sternums 1 for which the two sections 11, 12 are not adequately united.

FIG. 2A is a diagram of sternal dehiscence post-surgery in which the two sections 11, 12 of the sternum 1 are secured with wire fasteners 4. The spaces and gaps 3 are present, particularly in the inset. FIG. 2B is a diagram illustrating the two sections 11, 12 of the sternum 1 secured with plates and screws 5. Even though the sternum 1 is fused, potential complications resulting from the plates and screws include difficulty in separating the two sections 11, 12 should, for example, access to the heart is needed.

According to Wolff's Law, for bone to form properly and for the sternum to fuse shut, both time and compression (i.e. loading) needs to be present in the affected areas in which bone formation is desired. Wolff's Law states that bone in a healthy person or animal will adapt to the loads under which it is placed. The biology of fracture healing is a complex biological process that follows specific regenerative patterns and involves changes in the expression of several thousand genes. Bone healing, or fracture healing, is a proliferative physiological process in which the body facilitates the repair of a bone fracture. Primary healing (also known as direct healing) requires a correct anatomical reduction which is stable, without any gap formation. When a gap occurs, the lack of proper contact and compression along the sternal plane during closure is a significant contributing factor to dehiscence of the two sections 11, 12 and other post-sternotomy complications.

A serious complication associated with sternotomy may include the development of a deep sternal wound infection (DSWI), particularly within spaces left due to dehiscence of the two sections 11, 12 of the sternum 1. DSWI has up to a 6% incidence of occurrence after cardiac surgery and a potential high morbidity and/or mortality rate, which prolongs hospital stay and significantly increases cost of care. Early detection and aggressive treatment with debridement, drainage, and immediate wound closure using various mechanical methods are currently utilized and are necessary to prevent the development of sternal wound infection post-surgery.

Another complication may include post-operative pain experienced by the patient from paradoxical (i.e. abnormal) motion of the two sections 11, 12 of the sternum 1, for example, when edges of the two sections 11, 12 grind and/or rub together as the patient moves and/or micromovements of the two sections 11, 12 as the patient breathes. This pain can be problematic as it is impossible for a patient to remain completely motionless.

A long-lasting complication may include scar tissue formation. Because of the lack of proper closure and compression on the two sections 11, 12, scar tissue—rather than bone—may build up causing union of the two sections 11, 12 and thus stabilizing the sternum 1. The development and building up of scar tissue can be problematic, especially in situations in which further surgical intervention is necessary. The scar tissue often adheres to internal structures in addition to the sternum 1, such as cardiac blood vessels. If a surgeon needs to conduct additional surgery, the surgeon must first remove scar tissue covering the vessels. If the scar tissue is prevalent enough, the surgeon could easily cause injury to or even death of the patient during subsequent surgeries.

Post-operative sternal stability is an important consideration to avoiding and/or overcoming the aforementioned complications. Stability can be maintained by transverse fixation of the sternum 1 by using stainless steel wires 4 (for example as illustrated in FIG. 2A) and/or titanium plates 5 (for example as illustrated in FIG. 2B). However, in order to achieve such stability, proper preparation and stabilization of the sternum 1 is critical prior to closure of the incision. Preparation for closure utilizing grafting can significantly improve the chances for proper healing of the sternum 1 and/or substantially reduce the amount of post-operative pain experienced by the patient, thus leading to much quicker recovery rates.

Figure 3:
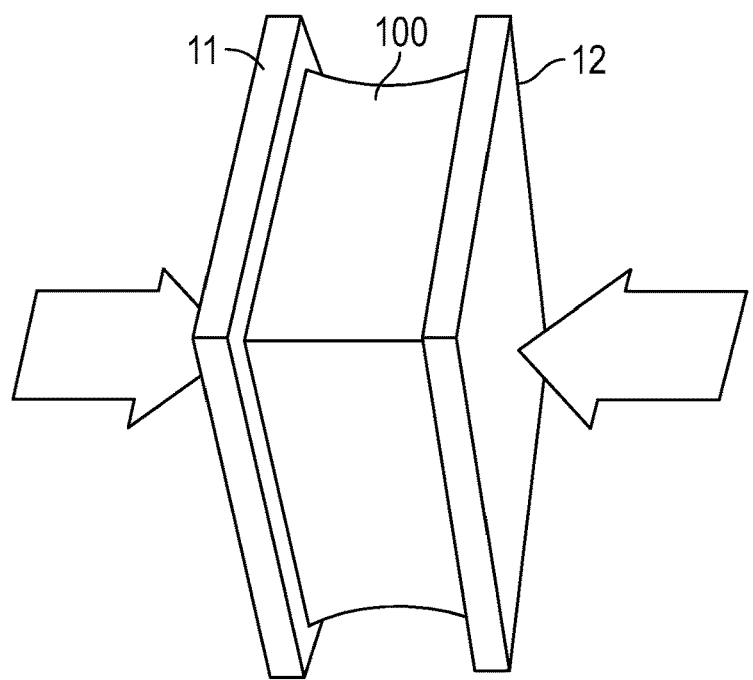
FIG. 3 is a diagram illustrating an implant disposed between two sections of a bone.

An implant 100 can dramatically improve sternal closure and post-operative sternal stability by providing an osteoinductive and/or osteoconductive "gasket" for sternotomy. For example, the implant 11 can function as a compressible packing closing any gaps between two separated sections 11, 12 of the sternum 1. FIG. 3 illustrates an exemplary implant 100 disposed between two separated sections 11, 12 of bone 1, such as the sternum 1. The implant 11 provides the "gasket effect," as the two sections 11, 12 are brought together as shown by the arrows. By filling/closing the gaps and/or spaces that accompany sternal closure, the chance of infection decreases, scar tissue formation is discouraged, and movement of the two sections 11, 12 is at least reduced to decrease post-operative pain. Furthermore, insertion of the implant 100 can significantly improve compression along the surface of the sternum 1. By acting as a gasket between the two sections 11, 12, the implant 100 can place a load on the surface areas of the two sections 11, 12. Accordingly, the environment for bone healing and new bone formation can be optimized according to Wolff's Law. Thus, the implant 100 can substantially reduce or eliminate the opportunity for development of sternal wound dehiscence. Further, given the objective of the surgeon to make up for bone loss in the sternum post sternotomy, the present inventive concept advantageously enables the surgeon to avoid altering the dynamic of the thoracic skeletal system, especially as it relates to the thoracic spine and the facet joints of the spine. A significant benefit to the present inventive concept is the fact that, as the surgeon wires the sternum back together and attempts to get sufficient compression, for example by tightening down wires with wire ties, the implant 100 not only functions as a bone gasket, but also functions to replace loss of tissue such as bone taken during access/sawing process of the sternotomy. The implant 100 can more than make up the gap created in the sternum during this process, while also providing proper compression to the sternal plane, which facilitates fusion, and maintaining proper body mechanics, especially as it relates to the thoracic spine and the thoracic spine facets. Without the present inventive concept, the surgeon inadvertently and artificially loads the facet joints of the thoracic spine in a manner that leads to early modic and degenerative changes in the articulating surface of the facet joints.

Figure 4:
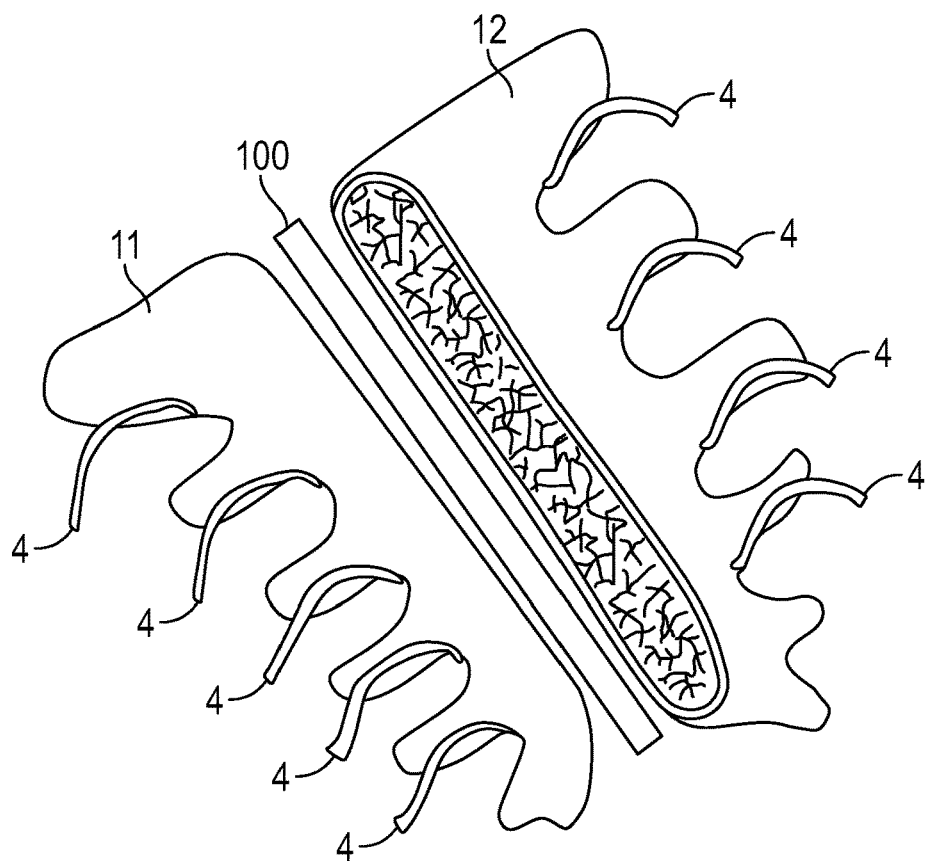
FIG. 4 is a diagram illustrating insertion and positioning of the implant into a space between the two sections of the sternum.
Figure 5:
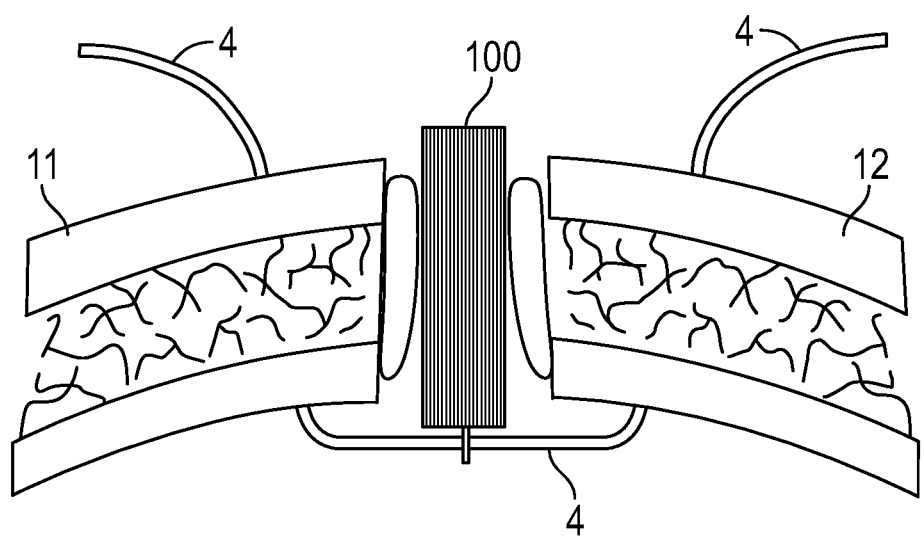
FIG. 5 is a diagram illustrating compression of the two sections of the sternum such that the implant abuts the two sections of the sternum and closes the space therebetween.

Insertion and positioning of the implant 100 into the space between two aligned sections 11, 12 of the sternum 1 is illustrated in FIGS. 4 and 5. The two sections 11, 12 are aligned with one another, and the implant 100 is positioned in between the two sections 11, 12. After insertion, as shown in FIG. 5, the two sections 11, 12 of the sternum 1 are brought towards one another and compressed such that implant 100 abuts the two sections 11, 12 of the sternum 1 and closes the space therebetween. Sternum 1 can then be securely closed using wire 4. In other examples, other methods of fastening can be utilized without deviating from the scope of the invention.

Figure 6:
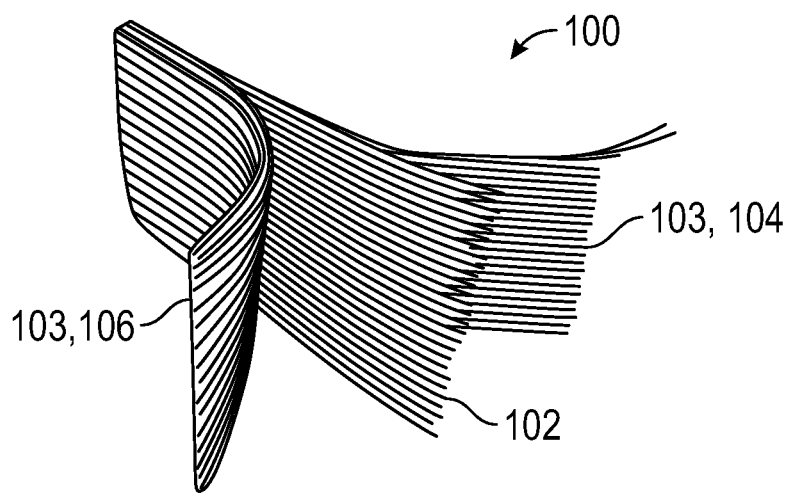
FIG. 6 is a diagram illustrating a partially exploded example of an implant.

FIG. 6 is a diagram illustrating a partially exploded example of an implant 100 operable to be disposed between and fuse two sections 11, 12 of a bone 1. The implant 100 can include an inner layer 102 and an outer layer 103 at least partially surrounding the inner layer 102 and operable to abut against the two sections 11, 12 of the bone 1. In at least one example, the inner layer 102 can include demineralized cortical bone graft, for example harvested from a donor or from the recipient's own bone. As illustrated in FIG. 6, the outer layer 103 includes a first portion 104 and a second portion 106. The inner layer 102 can be sandwiched between the first and second portions 104, 106 of the outer layer 103. The inner layer 102 and/or the outer layer 103 can include tissue. In at least one example, the inner layer 102 and/or the outer layer 103 can include at least a portion of at least one of the following: cortical bone fibers, cancellous bone fibers, collagen sponge, cortical bone graft, synthetic bone, and/or tissue graft. In some examples, the inner layer 102 and the outer layer 103 can be made of the same material(s) such that the implant 100 is globally made of the same material. In some examples, the inner layer 102 and the outer layer 103 can be made of different material(s). In at least one example, each of the first and second portions 104, 106 of the outer layer 103 can expand to at least three times the depth of inner layer 102. Accordingly, the outer layer 103 can expand and fill in any spaces between the two sections 11, 12 of the sternum 1.

Figure 7:
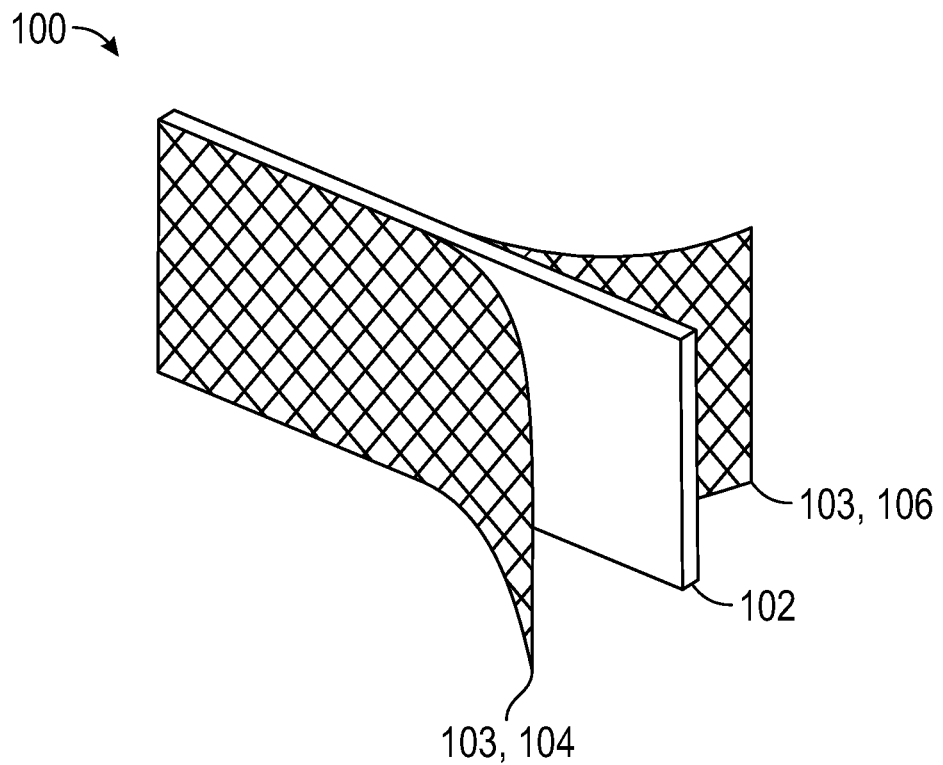
FIG. 7 is a diagram illustrating a partially exploded example of an implant.
Figure 8:
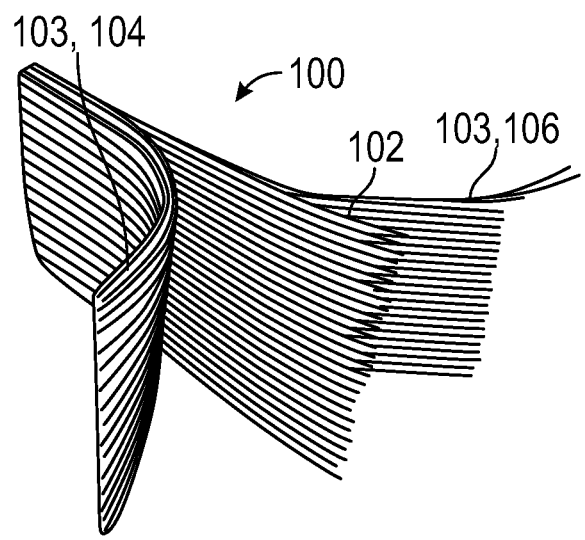
FIG. 8 is a diagram illustrating a partially exploded example of an implant.

FIGS. 7 and 8 illustrate another example of the implant 100. The implant 100, as illustrated in FIGS. 7 and 8 includes a spun bone wool sternal gasket harvested from human tissue. The implant 100 can be made of tissue. The implant 100 can be made from cortical bone, cancellous bone, dense cortical/cancellous bone, collagen fibers, and/or any number of other suitable human or animal bone derived tissues. In at least one example, the implant 100 can include at least one cellular growth factor. The cellular growth factors can include at least one of the following: bone morphogenetic proteins (BMPs), mesenchymal stem cells, blood, osteoclasts, osteoblasts, antibiotics, analgesics, and/or medications. In at least one example, blood can be drawn from the patient, spun down, and added or soaked into implant 100 so that the implant 100 becomes a carrier for the patient's own cells.

While the disclosure is focused on the implant 100 being used to fuse the two sections 11, 12 of the sternum 1 back together, for example following an open sternotomy procedure, the implant 100 can be used in other parts of the human body to aid in fusion, including, but not limited to the ankle, foot, knee, spine, hip and SI joints, shoulder, long bones, elbow, cranium, and maxillofacial repair without deviating from the scope of the invention.

In at least one example, the implant 100 can be porous and/or fibrous to receive at least one cellular growth factor such as the cellular growth factors discussed above. In some examples, the outer layer 103 is porous and/or fibrous and operable to receive at least one cellular growth factor. For example, the implant 100 can include spun bone which can make the implant 100 porous to allow blood and other fluids to easily pass through the bone fibers. This allows bone healing cells, osteoclasts and osteoblasts, naturally occurring bone morphogenic proteins and other cells, and/or added osteoconductive substances to incorporate easily throughout the implant 100. Additionally, the inclusion of the cellular growth factors can provide for significantly quicker and greater rates of healing and fusion. The fibrous nature of the implant 100, such as spun bone, can function to fill voids and also give flexibility and compressive characteristics to the implant 100.

The porous nature of the implant 100 can also provide flexibility. Thus, the implant 100 can have the ability to adapt easily to the natural contours of the body. Flexibility also can allow the implant 100 to overcome challenging bone structure either created by the surgeon upon accessing the chest cavity during entry or as a result of trauma, loss of bone, and/or other naturally occurring issues.

Another benefit of implant 100 is that it can be formed into a variety of shapes, sizes and thicknesses to enable the surgeon to cut or trim the implant 100 into smaller sections or pieces. In at least one example, particularly useful for sternal applications, the implant 100 can have the general shape of a rectangular parallelepiped in which the length has the longest dimension and the thickness has the shortest dimension so that the implant 100 can be placed against the incised wall of the sternum 1 where it will act as a "fusion gasket and/or void filler" to accomplish, among other things, at least one of the following actions.

Bone Fusion Gasket: the implant 100 can provide a fusion matrix, void filler, and/or gasket that can accelerate and promote fusion of the sternum following an open sternal procedure. This accelerated healing can promote bone fusion to occur and at least reduce the development of scar tissue. Often, patients develop scar tissue that forms after an open sternal procedure and not bone formation. Implant 100 promotes bone fusion and healing to occur.

Post-Op Pain Management: the implant 100 can act as a buffering platform to help reduce post-operative pain caused by coughing and movement. Since the chest wall moves when a patient coughs post-operatively, the ragged edges of the incised bone translates against itself. This translation can cause exposed and raw nerve endings to become severely irritated and can produce massive amounts of pain. The implant 100 can cushion, shield, and protect the exposed nerve endings and buffer the translational forces to significantly reduce post-operative pain.

Sternal Wound Dehiscence: sternal wound dehiscence is the condition that occurs when a patient's sternum gets infected after an open sternal procedure. The result is a very costly post-operative treatment with a 50% morbidity rate. Implant 100 can include a live cellular matrix that will promote bone formation and healing. In addition, implant 100 can act as a carrier for at least one cellular growth factor such as bone morphogenetic proteins, mesenchymal stem cells, blood, osteoclasts, osteoblasts, antibiotics, analgesics, and/or medications.

Spirometer Readings: post-operative breathing following an open sternal procedure can be very difficult and painful for the patient. Post-operative air capacity in the lungs is critically important for a patient to make a full and healthy recovery from surgery. Patients are reluctant to take full breaths following and open sternal procedure because it can be very painful. Pain is generated from the sternal incision as the chest wall "books" open and closed as the lungs inflate and deflate with breathing. Because the patients may be reluctant to take full breaths because of the pain, some patients develop pneumonia post operatively. The implant 100 can act as a dampening device and give the chest wall added cushion and material capacity to allow and encourage the patient to take deep, post-operative breaths. Thus, the implant 100 can help the patients increase their spirometer readings due to the reduction in pain as well as the added material aiding the chest wall in the expansion and contraction of the lungs.

Compression and Wolff's Law: As discussed above, bone needs two factors to fuse and heal appropriately, time and compression. Proper compression across the sternal plane post-operatively is extremely difficult to achieve because horizontal forces act on the sternum 1 rather than vertical forces. Gravity plays a very necessary role in proper bone healing and function. Gravity loads the skeletal system under normal conditions and this force allows bone cells to form and replace old cells. In the absence of gravity force, bone does not heal well or at all, which can lead to the development of soft tissue or scar tissue instead of bone fusion. When the bone has a vertical separation site, the forces of gravity may not distribute load adequately to such an separation site. Instead, the surgeon typically relies on using wire ties to close and give compression to the chest wall post-operatively. Since the wire ties are harder and denser that the surrounding bone, a surgeon cannot over tighten these wires as it will cause a stress riser against the bone and tear through the bone tissue upon excessive tightening. Because of this, the amount of horizontal compression applied to the wound is not adequate to satisfy Wolff's Law. There simply may not be enough compression applied to cause adequate fusion of the bone. In at least one example, the thickness of the implant 100 can compensate for any amount of bone lost, for example to the surgeon's sternal saw used to open up the patient. Typically, about 3 millimeters of bone may be lost to the width of the sternal saw. The thickness of the implant 100 can be thicker than the gap left by the saw. In at least one example, the implant 100 can be slightly oversized, flexible, and compressible. As the surgeon applies the wire ties or other mechanical sternal closure devices, the added material in the sternal wound from the implant 100 can be adequate to cause Wolff's Law to engage. Proper compression can now be achieved without excessive tightening of wire ties or closure devices.

As shown in FIGS. 7 and 8, the implant 100 can include an inner layer 102, for example including a shaved bone strip and/or a cortical bone graft, sandwiched between two portions 104, 106 of outer layer 103. The outer layer 103 can include fragmented, prepared, and spun cortical, cancellous and dense cancellous allograft or xenograft bone fibers. For example, the outer layer 103 can include the TRINITY tissue form available from Orthofix (Lewisville, Tex.) and MTF (Edison, N.J.).

Figure 9:
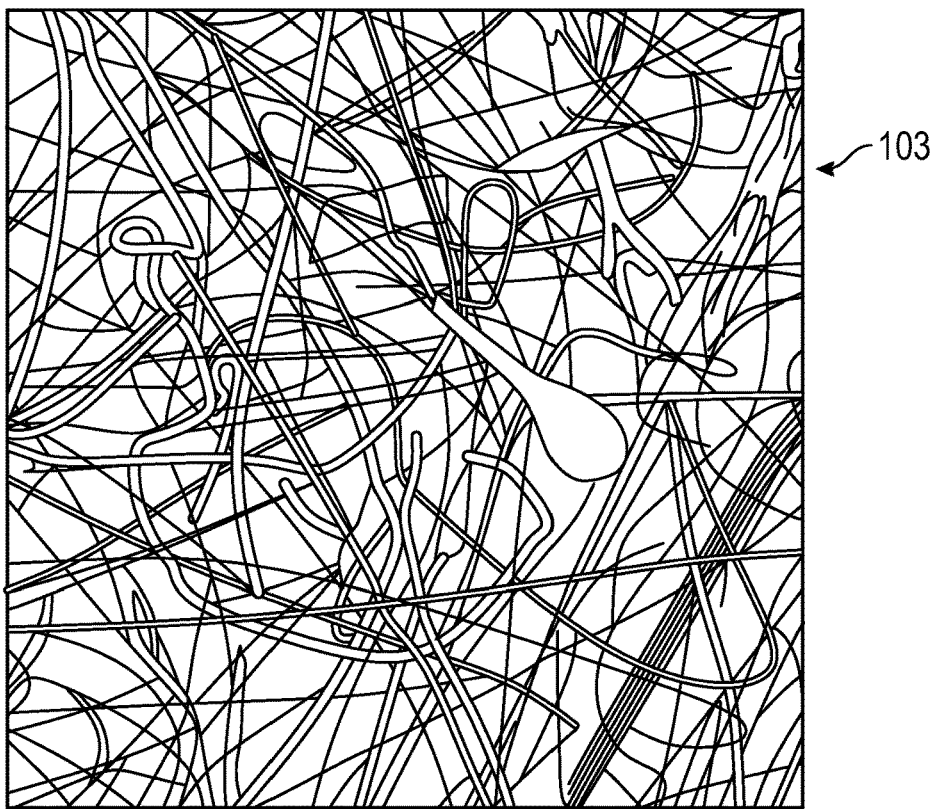
FIG. 9 is a diagram illustrating the porous nature of the outer layer.
Figure 10:
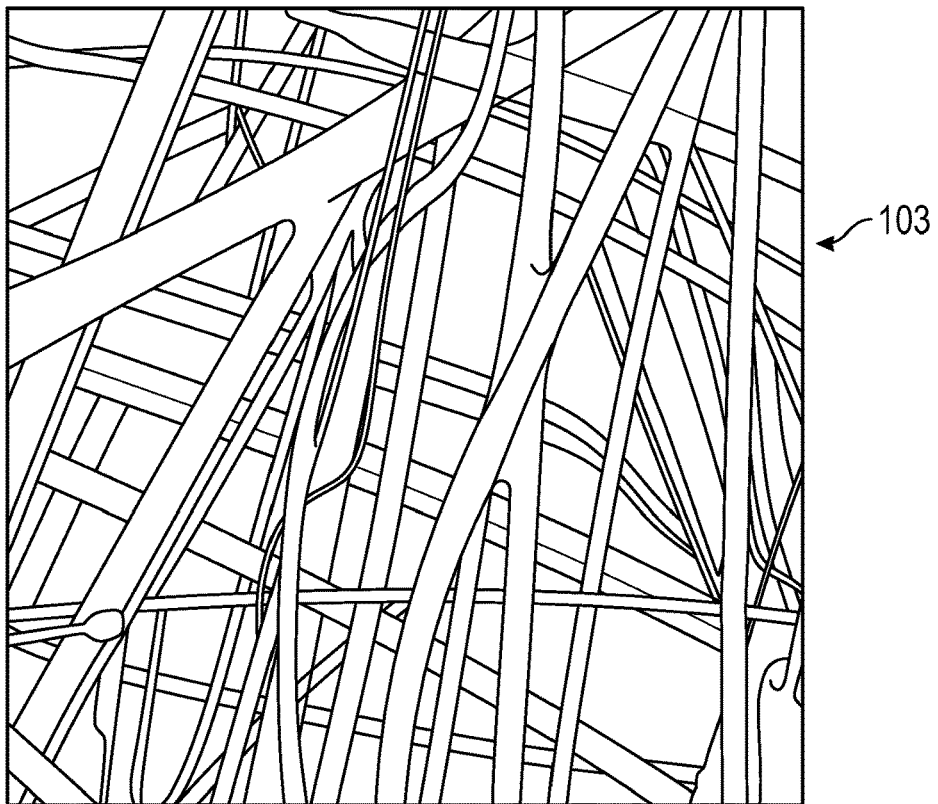
FIG. 10 is a diagram illustrating the porous nature of the inner layer.

FIG. 9 shows the porous nature of the outer layer 103. Shaved bone strip 103 can be an allograft or xenograft demineralized cortical bone graft harvested from a donor, or from the recipient's own bone. In at least one example, as illustrated in FIG. 10, the inner layer 102 can include a strip of bone that is also porous. The bone strip of the inner layer 102 can provide structural integrity. In at least one example, the inner layer 102 can be fenestrated to promote bony ingrowth.

As previously discussed, because of the porous and fibrous nature of implant 100, the implant 100 can act as a carrier for cellular growth factors such as, bone morphogenetic proteins, mesenchymal stem cells, blood, osteoclasts, osteoblasts, antibiotics, analgesics, and/or medications or materials a surgeon feels are appropriate to use in the treatment of the patient.

As illustrated in FIGS. 6-8, the inner layer 102 and the outer layer 103 are each substantially rectangular prism in shape. For example, the outer layer 103 can have substantially the same length as the inner layer 102. In some examples, the inner layer 102 and/or the outer layer 103 can be ovoid, spherical, wedge or shim (as illustrated in FIG. 13), and/or any other suitable shape without deviating from the scope of the inventive concept.

Figure 11:
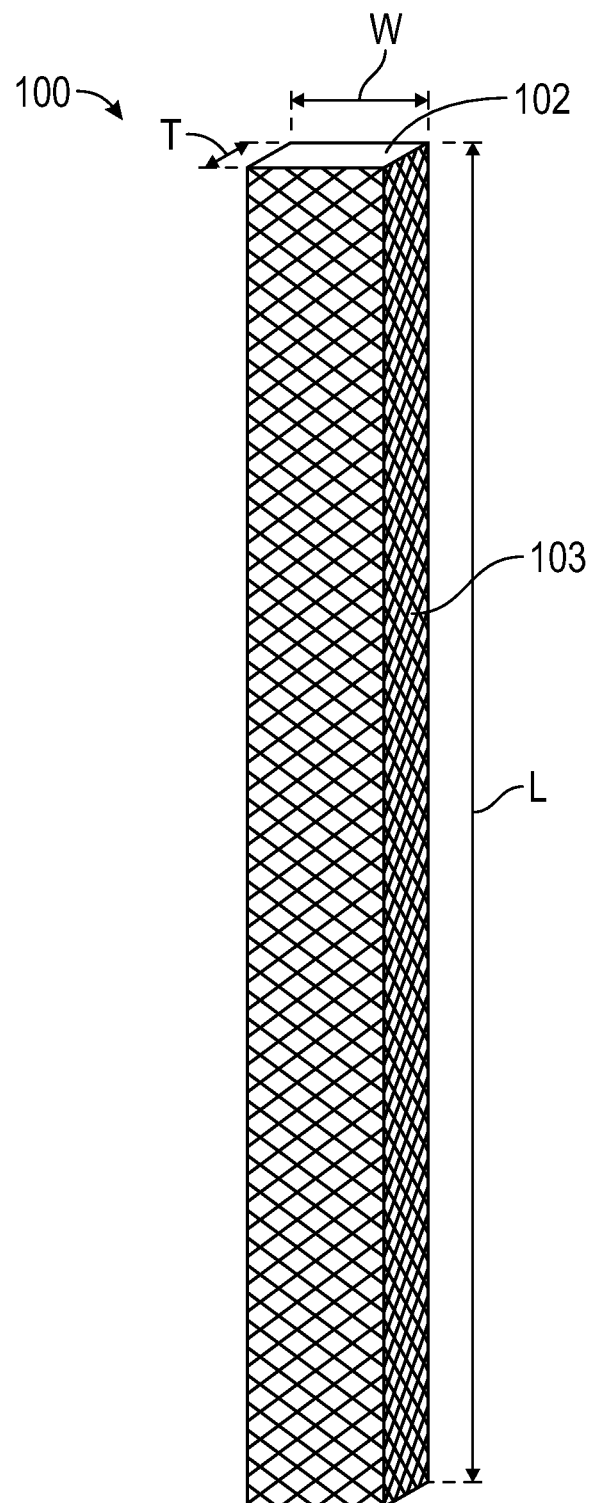
FIG. 11 is a diagram illustrating an example of an implant.

FIG. 11 illustrates an example of an implant 100 with a rectangular prism shape. Additionally, FIG. 11 illustrates an example of an implant 100 where the outer layer 103 is wrapped around a circumference of the inner layer 102. In at least one example, for example sternal applications, the implant 100 can have a thickness T from about 2 millimeters to about 100 millimeters, depending upon the anatomy of the patient and the preference of the surgeon. Alternately, the implant 100 can have a thickness T from about 2 millimeters to about 50 millimeters; alternately from about 2 millimeters to about 25 millimeters. In some examples, the implant 100 can have a thickness T from about 26 millimeters to about 50 millimeters. In some examples, the implant 100 can have a thickness T from about 51 to about 100 millimeters. In at least one example, the implant 100 can have a length L between about 7 inches and about 11 inches. Alternately, the implant 100 can have a length L of about 9 inches. In at least one example, the implant 100 can have a length L between about 25 millimeters and about 250 millimeters; alternately between about 25 millimeters and about 150 millimeters; alternately between about 25 millimeters and about 75 millimeters. In at least one example, the implant 100 can have a length L between about 76 millimeters and about 150 millimeters; alternately between about 151 millimeters and about 250 millimeters. The depth W of the implant 100 can be from about 0.5 inches to about 2 inches, again depending upon the anatomy of the patient and the preference of the surgeon. Alternately, the depth W of the implant 100 can be from about 1 inches to about 1.5 inches. In at least one example, the depth W of the implant 100 can be between about 1 millimeters and about 30 millimeters; alternately between about 1 millimeters and about 20 millimeters; alternately between about 1 millimeters and about 10 millimeters. In at least one example, the depth W of the implant 100 can be between about 11 millimeters and about 20 millimeters; alternately between about 21 millimeters and about 30 millimeters. In some examples, the implant 100 can be cut into segments to accommodate the different anatomy of each patient or to the preference of the surgeon.

Figure 12:
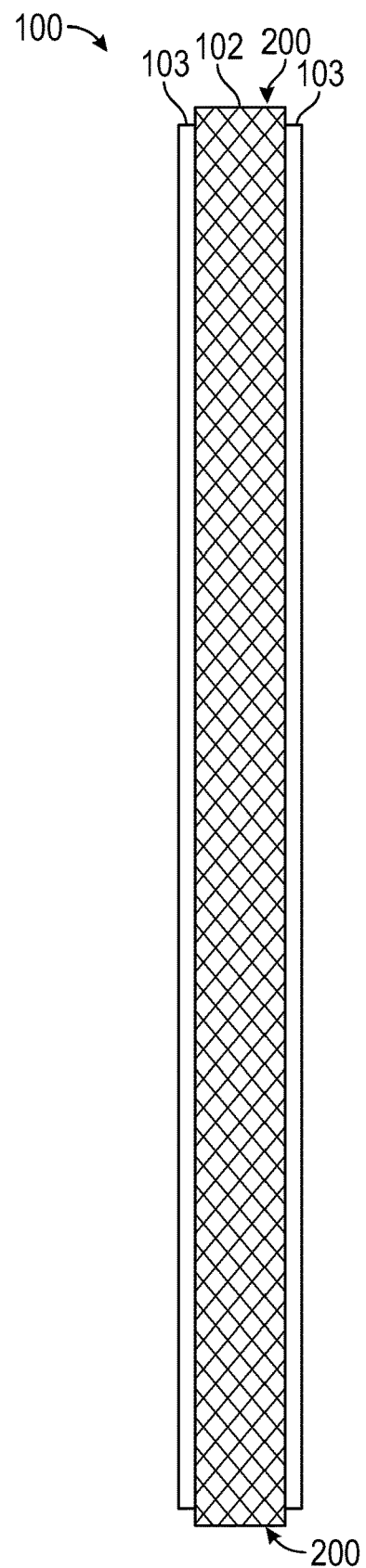
FIG. 12 is a diagram illustrating an example of an implant with flanges or tabs.

FIG. 12 shows another example of an implant 100. Similar to the implants 100 discussed above, the implant 100 illustrated in FIG. 12 includes an inner layer 102 and an outer layer 103 at least partially surrounding the inner layer 102. As illustrated in FIG. 12, the inner layer 102 is sandwiched between two portions 104, 106 of the outer layer 103. In at least one example, the inner layer 102 can be a denser form of the bone wool used in the outer layer 103. In other examples, the outer layer 103 can be denser than the inner layer 102. In at least one example, the inner layer 102 can be softer than the outer layer 103. In other examples, the inner layer 102 can be harder than the outer layer 103. In the implant 100, flanges or tabs 200 of the inner layer 102 can extend from the outer layer 103. While FIG. 12 illustrates flanges or tabs 200 extending from both sides of the outer layer 103, in some examples, the flanges or tabs 200 can extend from only one side of the outer layer 103. The flanges or tabs 200 of implant 100 can provide added compression and stability to help anchor along the incised edge of the sternum 1. The flanges or tabs 200 can create additional surface area and central compression along the incised sternal plane. This added feature helps ensure graft stability, position and integrity as the implant 100 is applied to the wound.

Figure 13:
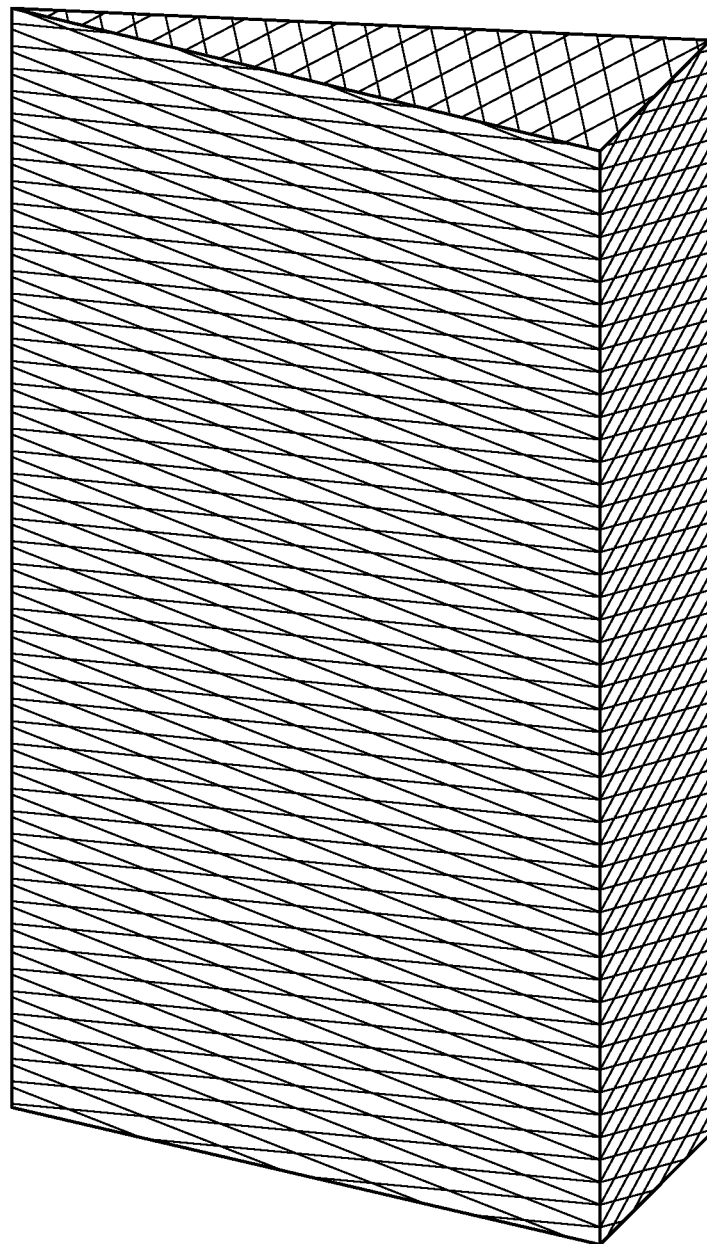
FIG. 13 is a diagram illustrating an implant in the shape of a wedge or shim.

FIG. 13 is a diagram illustrating an implant 100 in the shape of a shim. Implant 100, as a shim, provides added compression to the sternal plane once the sternal wires and or fusion gasket have been applied. The implant 100 can be cut, trimmed or otherwise shaped to size. The implant 100, in the shape of a shim, can be used to either augment additional implants 100 that may be the same or different shapes and/or sizes to provide compressive structure to areas where there are slight gaps between the outer layer 103 and the edge of the sternum 1. Alternatively, the implant 100 can be used as a stand-alone implant 100 of the desired shape and size to provide compressive integrity along the separated sternal plane. Accordingly, the implant 100 can create stability in the sternum 1 while providing the compression necessary to initiate fusion. Additionally, the implant 100 can help prevent the sternal wound "booking" during respiration as well as sternal wound "translation" during coughing episodes by minimizing or eliminating micro gaps that are created by sternal saws during the opening procedure.

It is foreseen for any example of the implant 100 that the implant 100 can be made of only the inner layer 102, only the outer layer 103, or a combination of the inner layer 102 and the outer layer 103. The combination may be a uniform combination of the inner layer 102 and the outer layer 103. In some examples, the inner layer 102 and the outer layer 103 can be made of the same material(s) such that the implant 100 is globally made of the same material. In some examples, the inner layer 102 and the outer layer 103 can be made of different material(s).

Compression across the sternal plane can be achieved in order to create fusion. The implant 100 can provide the desired compression by making up the gap upon access into the chest cavity. For example, the sternal saw can cause a gap of about 3 millimeters. By providing a greater amount of bone material along the vertical axis of the incised sternum 1, as the surgeon brings the two sections 11, 12 of the split sternal bone back together with the wire ties, the surgeon no longer needs to make up the gap left by the sternal saw. The implant 100 can bridge that gap and provide more bone material to initiate fusion due to the compression being exerted on the two sternal sections 11, 12 which not previously available with wire closure alone.

The basic technique of wiring the sternum closed has not changed or been truly examined since its inception in the 1950's. Cardiovascular surgeons are soft tissue specialists—not orthopedic specialists. Their current gold standard technique of sternal closure isn't functional for bone healing and the long-term health of the patient. The wound created to access the chest cavity can be the most problematic aspect of the entire procedure. Therefore, viewing the treatment and closure of the sternum as a "reconstruction" is vital to the success, safety and health of the patient. Therefore, implant 100 is being termed and viewed as a Sternal Reconstruction Technology because of the nature of what it's achieving in the wound and the ultimate goal of the technique. True bone healing requires that the conditions for cell proliferation leading to bone formation via fraction, repair and remodeling be met. By adding the implant 100 into the incised sternal wound, proper compression and exposure to a bone fusion catalyst can be achieved.

Figure 14:
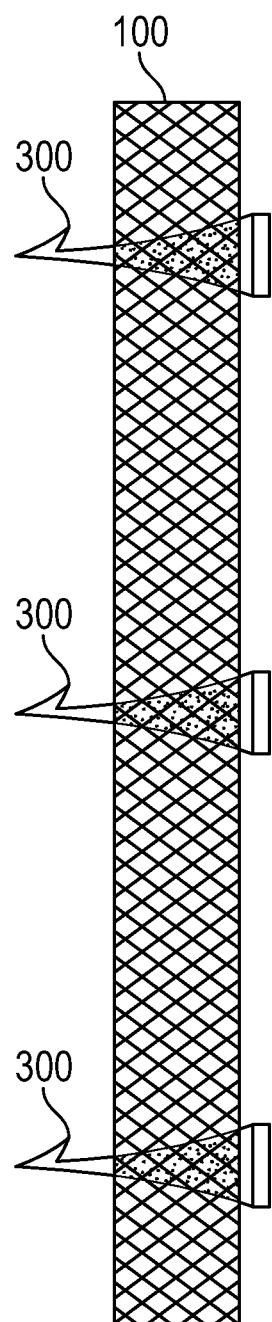
FIG. 14 is a diagram illustrating an implant including fasteners or tacks.

In some examples, fasteners 300 can be used for fixation, improved sternum positioning, and alignment. In at least one example, the fasteners 300 can couple the implant 100 to the edge of, and/or insert the implant 100 at least partially within, the sternum 1 upon initial implantation. FIG. 14 illustrates an implant 100 with fasteners 300. The fasteners 300 as illustrated in FIG. 14 extend from inner layer 102 and/or the outer layer 103 of the implant 100 and are operable to couple with the bone 1. The fasteners 300 may be made of a hard material to couple with the bone 1, while the inner layer 102 and/or the outer layer 103 of the implant 100 may be a soft, malleable, and/or spongy material to fill in any voids in the bone 1. FIG. 14 shows that the implant 100 includes three fasteners 300 extending therefrom. In other examples, one, two, or more than three fasteners 300 can be included without deviating from the scope of the invention.

Figure 15:
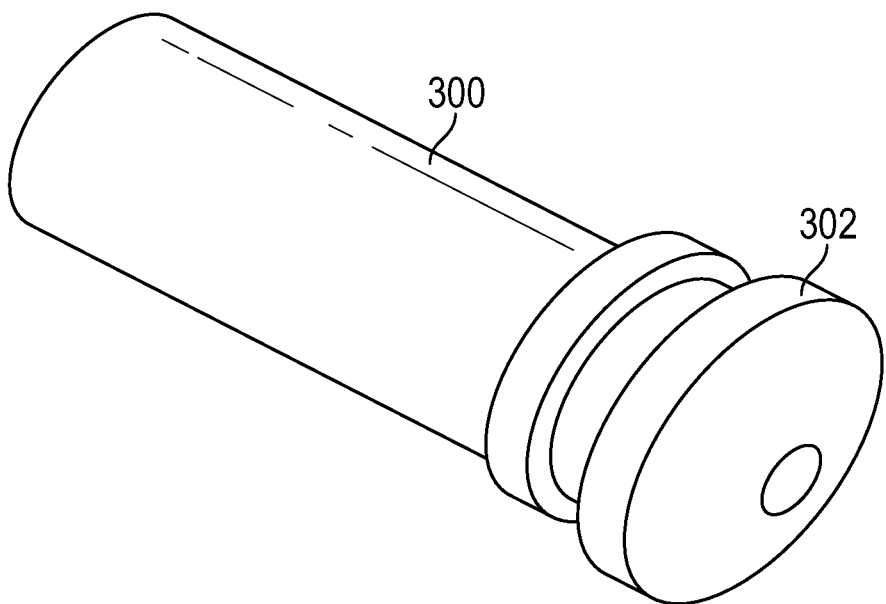
FIG. 15 is a diagram illustrating an example of a fastener.
Figure 16:
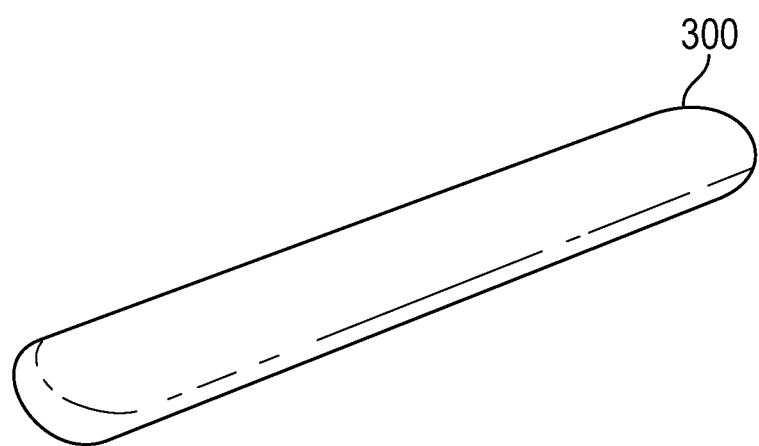
FIG. 16 is a diagram illustrating another example of a fastener.

As illustrated in FIG. 14, the fasteners 300 are tacks with hooks operable to be inserted into the bone and couple the implant 100 with the bone. FIG. 15 illustrates a fastener 300 with a head or cap 302 where the head or cap 302 has a width or diameter larger than the body of the fastener 300. In some examples, the head or cap 302 can be made of allograft bone. In other examples, the head or cap 302 can be made of any material that the fastener 300 can be made of without deviating from the scope of the invention. FIG. 16 illustrates a fastener 300 in the shape of a pin where the fastener 300 does not include a head or cap. Accordingly, the fastener 300 as illustrated in FIG. 16 has substantially the same thickness. Additionally, as illustrated in FIG. 16, the fastener 300 can have ends that taper and/or are rounded.

Figure 17:
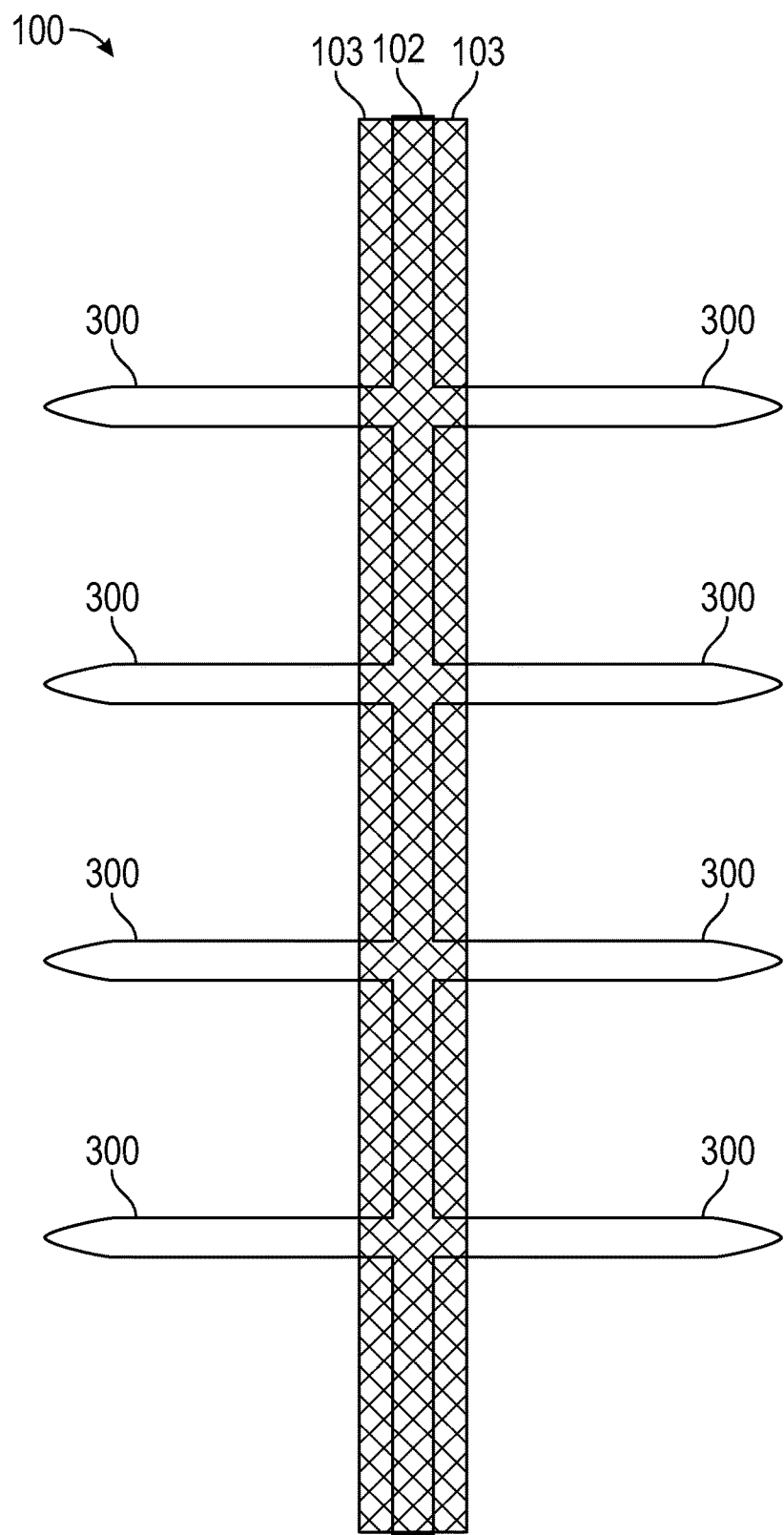
FIG. 17 is a diagram illustrating an implant with bone cross-pins.

As illustrated in FIG. 14, fasteners 300 extend from the implant 100 on one side only. In at least one example, as illustrated in FIG. 17, fasteners 300 can be included and extend from the implant 100 on both sides. The purpose of this cross-pinning, like that of the use of fasteners 300 on one side, is to provide a structural format that will allow implant 100 to function, for example, in at least one of the following manners:

1. To provide a structural, ridged platform that is coupled with the outer layer 103 that acts as a compressive gasket. This design can enhance stability in the sternum 1 while providing the compression necessary to initiate fusion.
2. To prevent the sternal wound from booking open and closed, for example during respiration. This can lead to scar tissue formation and/or sternal dehiscence.
3. To prevent wound translation. Wound translation can occur when the two sections of the bone rub back and forth against each other. For example, the patient may cough post operatively and cause the sternal edges of the wound to rub back and forth against each other. The use of fasteners 300 can reduce the translational forces, for example caused by coughing, movement, and/or breathing. Reducing the translational forces can lead to significantly reduced levels of pain, reducing the need for post-operative pain drugs, reduced time in the ICU, and/or recovery days spent in the hospital.
4. To add structural integrity back into the bone. In at least one example, such as with a sternotomy, this can be considered a reconstructive operative measure the surgeon is taking. The added strength and stability can encourage faster healing rates due to the fact that motion will be reduced across the bone, for example the incised sternal plane.

In at least one example, to fix the implant 100 in place along the incised sternal plane, the surgeon can take any combination of the following steps:

1. Clean the edges of the sternum from excess soft tissue.
2. Measure the length of the edge of the sternum and cut implant 100 to size, if necessary or desired.
3. Use an awl to punch holes in the sternal edge on one side as to where the surgeon wants to fix implant 100 in place, if necessary or desired.
4. Once the holes are created, the surgeon can pierce implant 100 with tack 300 and then press fit tack 300 and the attached implant 100 into place along one sternal edge.
5. The sternum can be closed, for example using wiring techniques. As the wires are cinched down and tightened, implant 100 is compressed between the two incised edges of the two sections of the sternum. This process then secures implant 100 in place and helps create the compression needed for bone growth.

The fasteners 300 can be made of one or more of the following:

1. Human Donor Bone—Allograft Tissue
2. The Patients Own Bone—Autograft Tissue
3. Animal Bone—Xenograft Tissue
4. Materials such as tissue for example bone tissue, vicryl, polypropylene, stainless steel, titanium, polyether ether ketone (PEEK), polyetherketone (PEK), polymers, metals, poly(methyl methacrylate) (PMMA), and/or various suture and suture materials. For example, the fasteners 300 can be formed using 3D printed material or any version of the tissue. Other methods of forming the fasteners 300 can be utilized without deviating from the scope of the invention.

Figure 18:
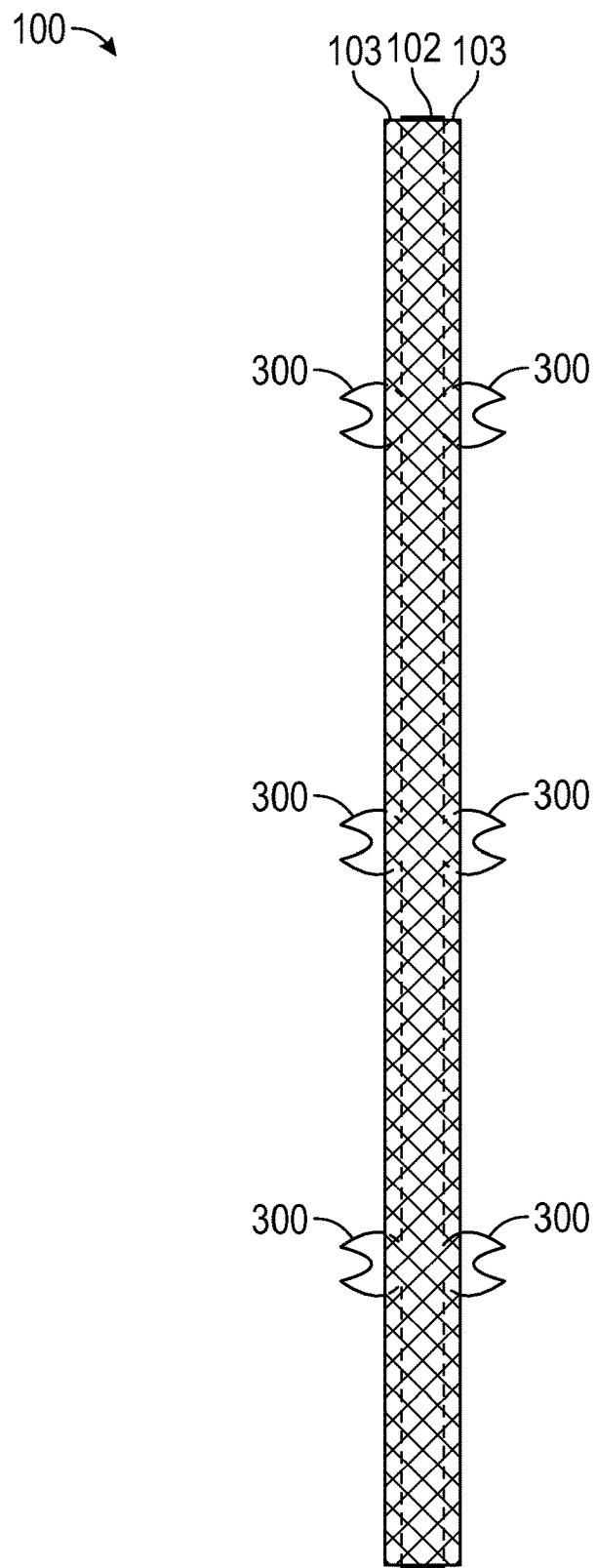
FIG. 18 is a diagram illustrating an implant with fasteners that include teeth or barbs.

As shown in FIG. 18, the fasteners 300 can include teeth or barbs. The implant 100, as illustrated in FIG. 18, includes an inner layer 102 enclosed within an outer layer 103. The outer layer 103 includes teeth or barbs 300 that are integral to the inner layer 102 and/or coupled with the inner layer 102. The length of the teeth or barbs 300 is selected so that the teeth or barbs 300 extend through the outer layer 103. In some examples, the teeth or barbs 300 can extend through the outer layer 103 only when the implant 100 is compressed into place. In other examples, the teeth or barbs 300 can extend through the outer layer 103 even in the absence of compression. The location, shape, and/or size of the teeth or barbs 22 can be varied without deviating from the scope of the invention.

In at least one example, the implant 100 can include a plurality of interlocking implants. The implants may include one or more modular implants. In at least one example, the implant 100 can include a plurality of interlocking, modular implants. By providing interlocking implants 100, a plurality of implants can be provided and interlocked to fill in any desired size and/or shape of voids in the bone 1. In some examples, the interlocking implants can include the same materials and/or features such that the size and/or shape of the implant 100 is as desired. In some examples, the interlocking implants may include different materials and/or features such that specific areas are targeted as desired.

Figure 19:
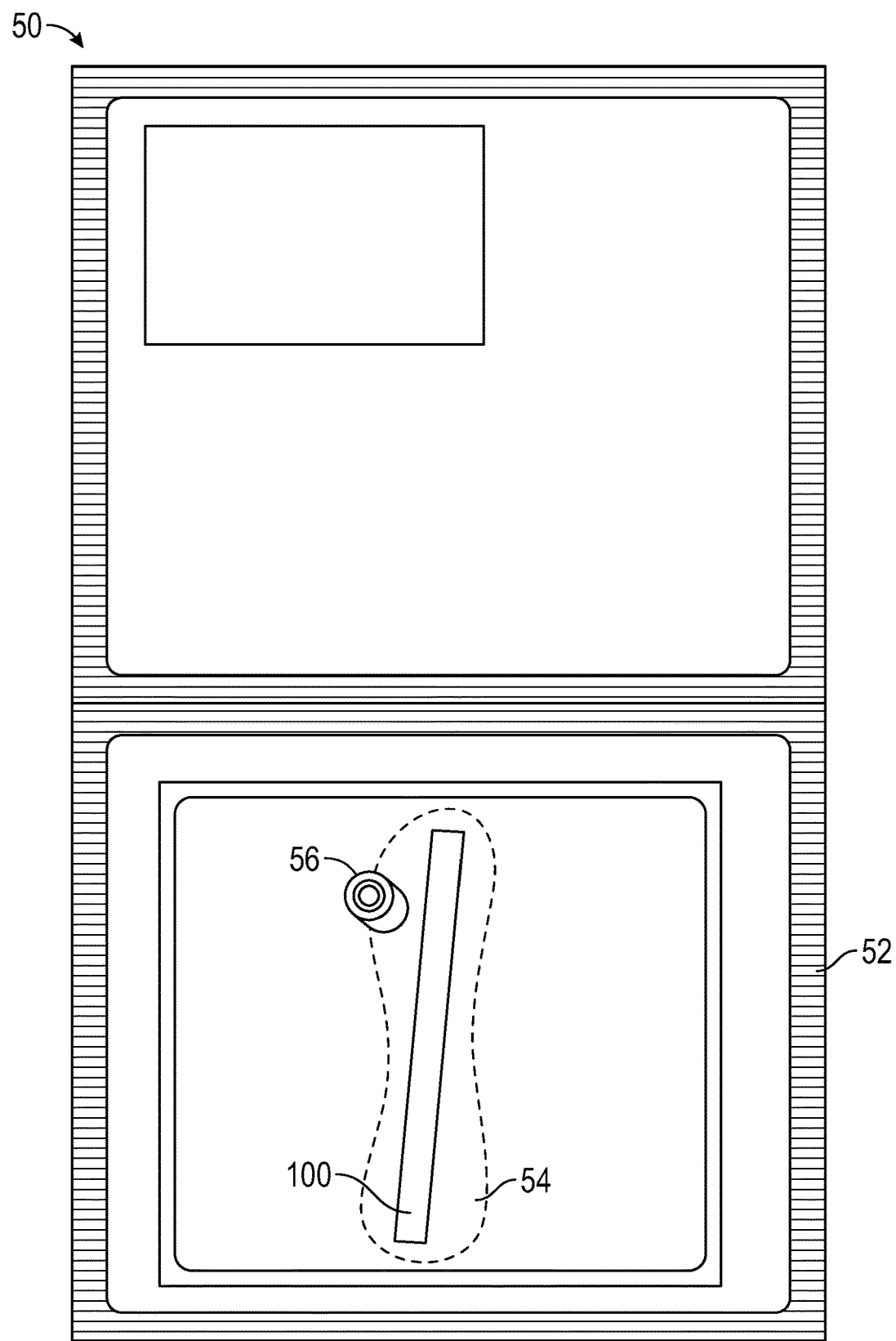
FIG. 19 is a diagram illustrating a sealed double peel-pack.

Any of the implants 100 and features discussed above can be provided in any suitable sterile surgical packaging. FIG. 19 illustrates a double peel pack 50. Pack 50 can package any of the implants 100 discussed above. As illustrated in FIG. 19, in addition to the standard seal providing the contents in a sterile environment, pack 50 includes a secondary seal 52 that includes a well or pouch 54 in which the implant 100 is contained. In at least one example, the secondary seal 52 can include an injection port 56 above or in close proximity to the well 54. Injection port 56 can be a luer lock connection so that a syringe can be coupled to the injection port 56 and be in fluid communication with the well 54. In other examples, the injection port 56 can be an area that is penetrable by an injection needle. The area can be made of a material (such as the materials used for medicine vials) that resists tearing or ripping after needle penetration. In at least one example, the injection port 56 can "re-seal" after needle penetration such that fluid does not flow through the injection port 56 after the needle is removed. Pack 50 provides a protected, sterile environment in which the user can safely and effectively deliver a fluid (such as platelet rich plasma or any other suitable cellular growth factors) to the well 54 to hydrate the implant 100. Secondary seal 52 provides protection and restricts fluidic communication to and from the well 54 to allow the hydration process to occur for the desired time.

Figure 20A:
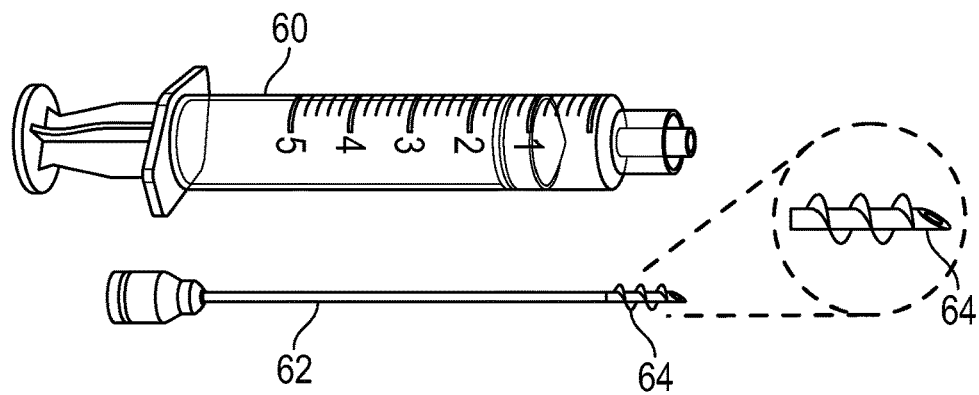
FIGS. 20A-C are diagrams illustrating a syringe with a needle having an auger-style tip being used to inject fluid into a double peel-pack.
Figure 20B:
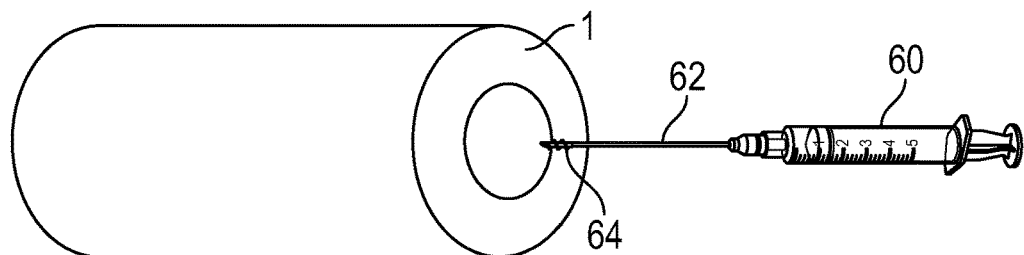
Figure 20C:
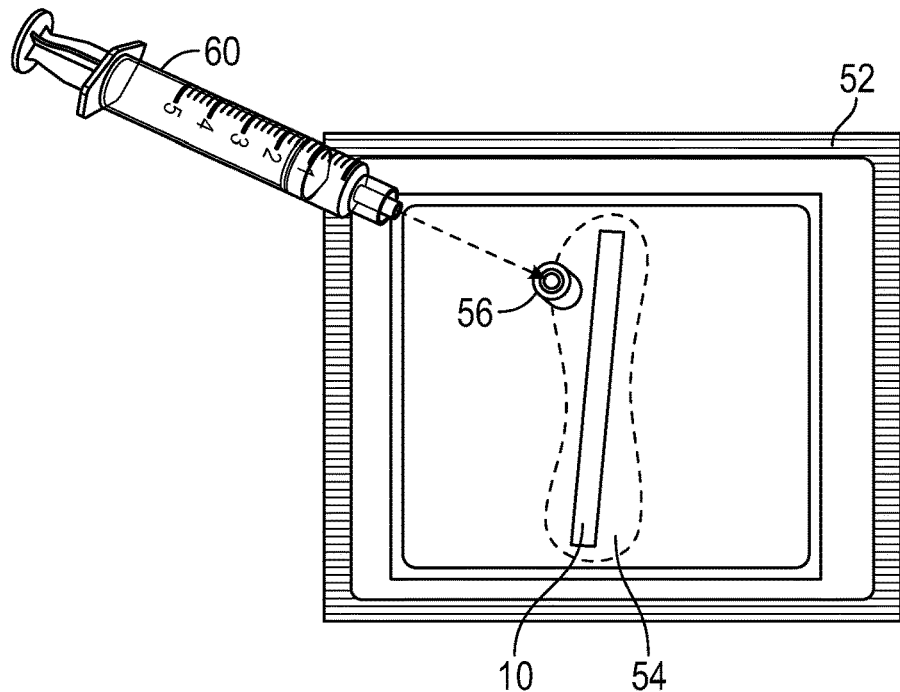

In at least one example, bone marrow aspirate can be used to hydrate bone graft implants 100. FIG. 20A illustrates an aspirating syringe 60 with a needle 62 having an auguring tip 64. As illustrated in FIG. 20B, the auguring tip 64 can be used to tap into the edges of the sternum 1 (or the bone marrow to be aspirated) with the specifically designed auguring effect to draw blood and cells out of this stem cell rich environment to utilize with the implant 100. Advancing the needle tip or otherwise changing the location of the tip (for example every 2 cc's of aspirate) can optimize retrieval of live cells. Although syringe 60, needle 62, and auguring tip 62 are designed to be used with and packaged with pack 50, syringe 60, needle 62, and/or auguring tip 62 can be used without pack 50. As illustrated in FIG. 20C, the injection needle 60 is inserted into the injection port 56. The injection needle 60 can deliver a fluid, such as platelet rich plasma to hydrate the implant 100 within the well 54.

As is evident from this disclosure, bone contact and minimization of motion between the implant 100 and the two sections 11, 12 of the bone 1 is important to promote fusion and to also achieve optimal clinical results. FIGS. 21-24 show possible surface modifications to reduce slipping and increase friction.

Figure 21:
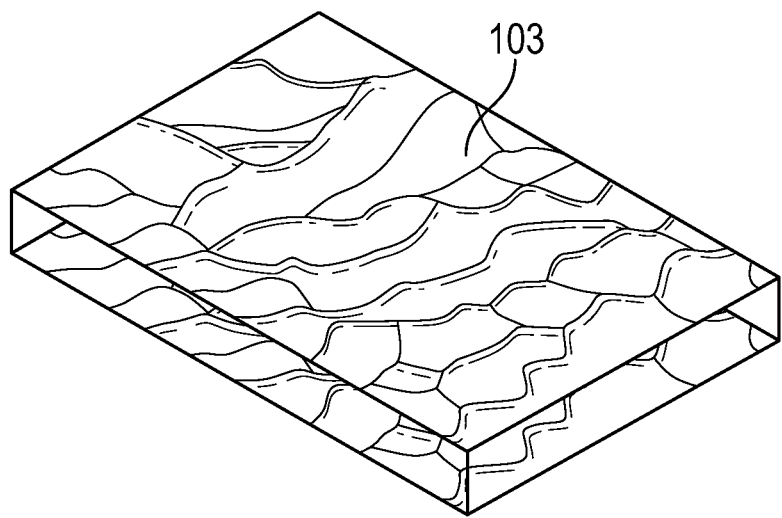
FIG. 21 is a diagram illustrating a surface treatment for an implant.

FIG. 21 illustrates that the outer layer 103 can include scalloping. In at least one example, as illustrated in FIG. 21, the scalloping can be asymmetric. In other examples, the scalloping can be symmetric.

Figure 22A:
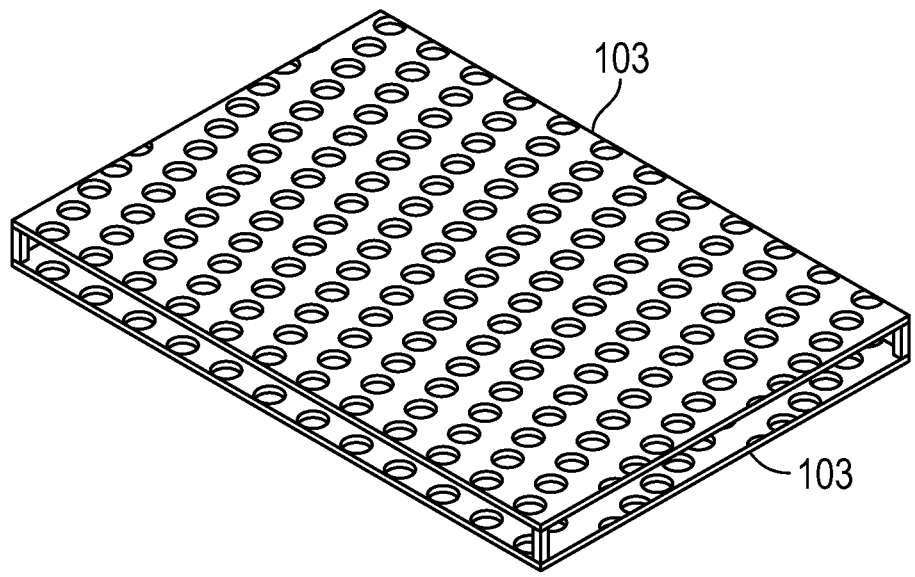
FIGS. 22A-C are diagrams illustrating a surface treatment for an implant.
Figure 22B:
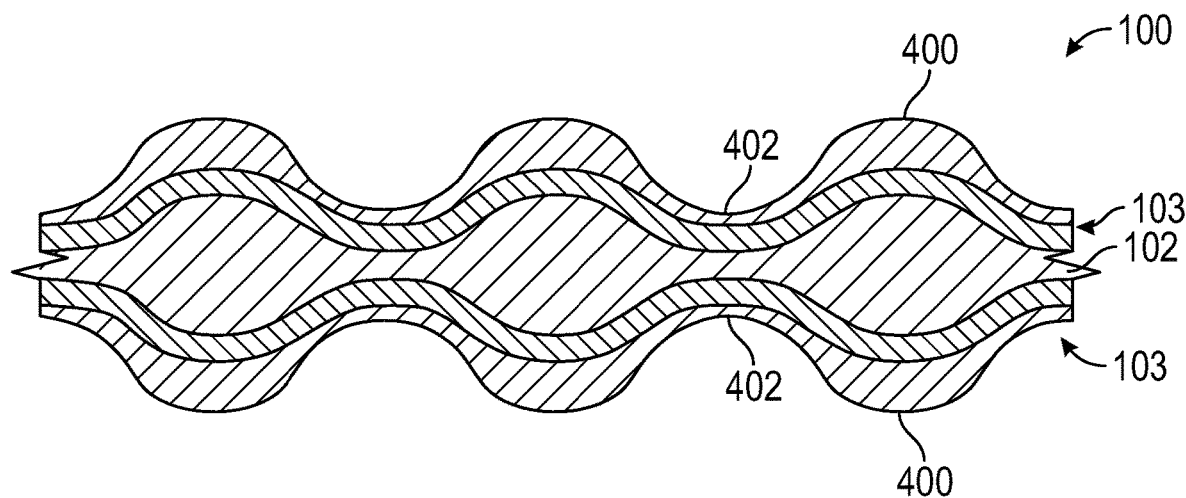
Figure 22C:
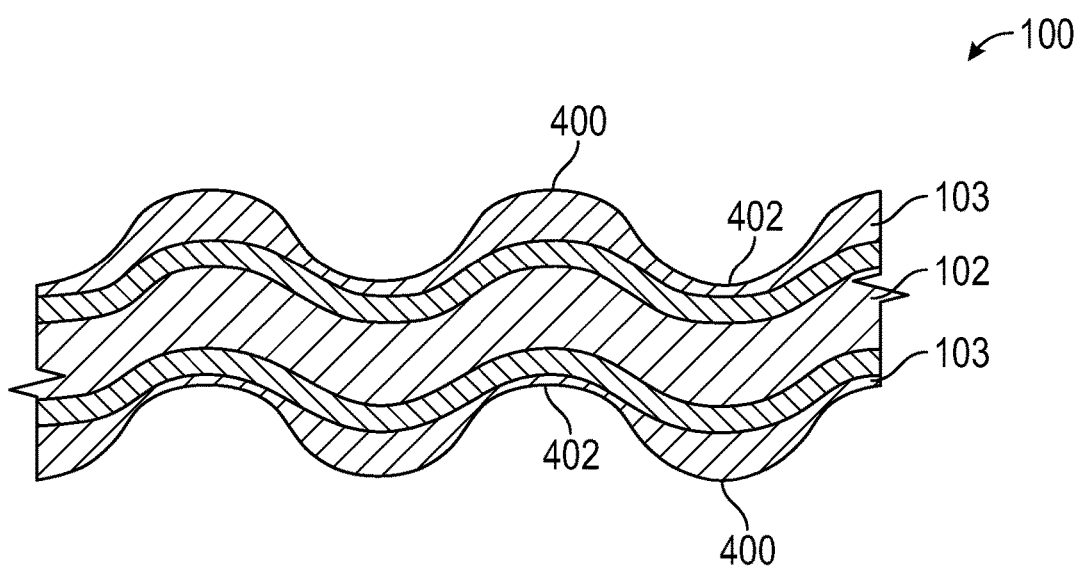

FIGS. 22A-22C illustrate microdimpled surface treatment of the outer layer 103. Opposing portions of the outer layer 103 can be dimpled, with the optimized dimpling of the surface divots 402 enhancing the compressibility of the material when deployed as a biological gasket. The surface divots 402 create mesas 400. In at least one example, as illustrated in FIG. 22B, the surface divots 402 and the mesas 400 can mirror one another. In some examples, as illustrated in FIG. 22C, the surface divots 402 and the mesas 400 can alternate.

Figure 23A:
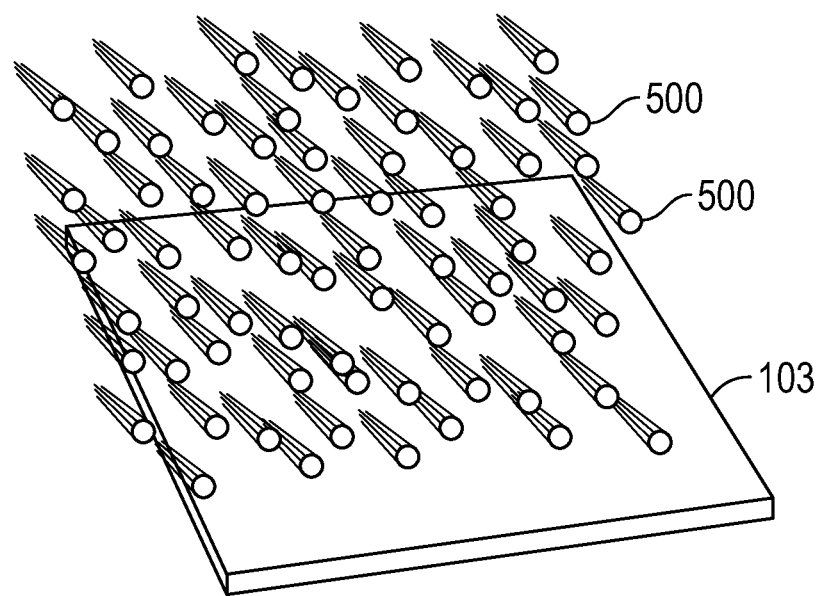
FIGS. 23A and 23B are diagrams illustrating a surface treatment for an implant.
Figure 23B:
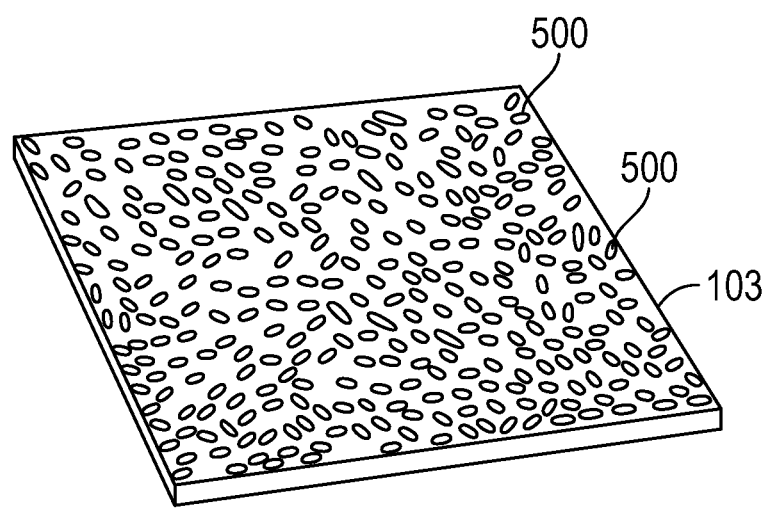

FIGS. 23A and 23B illustrate peening and embedding of beads 500 into the outer layer 103. In at least one example, the beads 500 can include micronized bone. In some examples, the beads 500 can include hydroxyapatite ceramics. While the beads 500 illustrated in FIGS. 23A and 23B are spherical, the beads 500 can be any other suitable shape without deviating from the scope of the invention. The beads 500 are velocity-driven to be embedded into the outer layer 103.

FIGS. 24A-C illustrate high velocity peened surface treatment. The surface of the outer layer 103 can be embedded with beads 600. The beads 600 can include at least one of the following: nano hydroxyapatite, micro hydroxyapatite, and/or micronized cortical bone. While the beads 600 illustrated in FIGS. 24A-C are spherical, the beads 500 can be any other suitable shape without deviating from the scope of the invention. As illustrated in FIG. 24B, the beads 600 are embedded into the surface of the outer layer 103 by high velocity peening. The high velocity peened surface treatment can provide a surface friction advantage as illustrated in FIG. 24C.

Other suitable surface modifications or treatments other than those specifically shown in FIGS. 21-24C can be utilized without deviating from the scope of the invention. Additionally, any combination of surface modifications can be utilized without deviating from the scope of the invention.

Referring to FIG. 25, a flowchart is presented in accordance with an example embodiment. The method 2500 is provided by way of example, as there are a variety of ways to carry out the method. The method 2500 described below can be carried out using the configurations illustrated in FIGS. 1-24C, for example, and various elements of these figures are referenced in explaining example method 2500. Each block shown in FIG. 25 represents one or more processes, methods or subroutines, carried out in the example method 2500. Furthermore, the illustrated order of blocks is illustrative only and the order of the blocks can change according to the present disclosure. Additional blocks may be added or fewer blocks may be utilized, without departing from this disclosure. The example method 2500 can begin at block 2502.

At block 2502, an implant 100 is disposed between two sections 11, 12 of a bone 1. In at least one example, the bone 1 can be a sternum. In some examples, the bone 1 can be any bone 1 which has been separated and/or fractured. The implant 100 can include an inner layer 102 including a cortical bone graft. The implant 100 can also include an outer layer 103 at least partially surrounding the inner layer and operable to abut against the two sections 11, 12 of the bone 1. The inner layer 102 and/or the outer layer 103 can include tissue. In at least one example, the inner layer 102 and/or the outer layer 103 includes at least a portion of at least one of the following: cortical bone fibers, cancellous bone fibers, collagen sponge, cortical bone graft, synthetic bone, and/or tissue graft. The outer layer 103 is porous and/or fibrous and operable to receive at least one cellular growth factor. The at least one cellular growth factor can include at least one of the following: bone morphogenetic proteins, mesenchymal stem cells, blood, osteoclasts, osteoblasts, antibiotics, analgesics, and/or medications. In at least one example, the implant 100 is soaked in the at least one cellular growth factor prior to being disposed between the two sections 11, 12 of the bone 1.

In at least one example, the implant 100 can have a thickness between about 2 millimeters and about 100 millimeters. In at least one example, the implant 100 can have a length between about 25 millimeters and about 250 millimeters. In at least one example, the implant 100 can have a depth between about 1 millimeters and about 30 millimeters. In some examples, the implant 100 can be cut to a predetermined thickness, length, and/or depth.

At block 2504, the implant 100 can be compressed between the two sections 11, 12 of the bone 1 such that the outer layer 103 is abutting against the two sections 11, 12 of the bone 1. In some examples, the implant 100 can be coupled with the bone 1 by inserting one or more tacks 300 extending from the outer layer 103 into the bone 1. The one or more tacks 300 can include at least one of the following: tissue, vicryl, polypropylene, stainless steel, titanium, polyether ether ketone (PEEK), polyetherketone (PEK), polymers, metals, poly(methyl methacrylate) (PMMA). In at least one example, the tissue can include bone tissue.

At block 2506, the compression of the implant 100 and the two sections of the bone 1 is secured. In at least one example, the compression can be secured using wires. In some examples, the compression can be secured using fasteners.

Clinical Evaluation

Design

The study was proposed as a multicenter, observational study. The study objective was to evaluate an interventional "gasket" (any of the implants disclosed herein) for repair of sternotomy wounds. Patient endpoints were defined as the proportion of subjects with related adverse effects. Data was represented after enrollment with follow-up of 60 patients with comparison to literature-reported rates for surgical complications including dehiscence, infection, and pain.

Methods

Patients undergoing open cardiac procedures at participating centers were considered for enrollment and included if consent was obtained (n=60 patients at 3 centers). Patients were followed during hospitalization and at a single, post-operative visit.

Experimental Approach

Dehiscence of median sternotomy wounds remains a clinical problem. Many solutions have been developed to reduce micromotion, bridge solid bone, strengthen fixation, and reduce risk in populations who have undergone cardiac surgery. Wire cerclage closure of sternotomy is the standard of care despite substantial evidence of pathologic sternal displacement (>2 mm) with normal physiologic strain, i.e. coughing. Post-operative functional recovery, respiration, pain, sternal dehiscence, and infection are influenced by early bone stability. This study was proposed to enhance the stability of conventional sternal closure post-cardiotomy. The remedy was aligned to demonstrating that a flexible bone graft will double the cross-sectional area of sternal fixation site, supplement if not replace the bone removed during the sternotomy, and/or accentuate healing while reducing complications. Methods addressing instability can involve plating, wiring, cinching, grafting, with and without muscle flap coverage.

A common technical shortcoming in closing sternotomies is the misalignment of the two sections 11, 12 of the sternum 1. In a study of patients subjected to sternal scanning in early postoperative period, good alignment, as well as proper contact of the sternal layers, was an exception rather than a rule. Dislocation of the sternum in either the antero-posterior or in the longitudinal dimension was common, as well as sternal spacing. The sternal approximation judged as "perfect" in only 15% of cases when wires were used, and none when the sternum was united with bands.

Recognizing that sternal stability and alignment are both factors that define outcome, the implant 100 as disclosed herein takes advantage of a functional "biological gasket" to increase the interface of the two sections 11, 12 of the sternum 1 and can, inter alia, reduce micromotion during healing.

Rationale

The underlying concern for stabilizing sternotomy closure is a discussion of fracture repair. Division of the sternum 1, even as a controlled surgical procedure, still required biological repair to consolidate the bone from either side of the sternum. Wires can be used as a low-cost method of reducing the fracture and supporting the mechanical conditions of healing. Wires offer the advantage of cohesive force in drawing the two surfaces together. Several factors influence the outcome: strength of the suture material; number, location, and placement of the sutures; and the tightness and applied stress (force/area) exerted. Unfortunately, sternal disruption can occur due to the mechanical action of the respiratory muscles and the negative intra-thoracic pressures associated with normal respiration. The implant 100 places a structured "gasket-like" material between the hemi-sternabrae during the repair that will be compressible, double the relative surface areas of the healing bone, provide a source of osteoinductivity and osteoconductivity, and replace the kerf of the tissue, for example bone tissue, that was lost during the cutting.

Bone repair and remodeling depends on the ensuing loading conditions. In fracture fixation, bone fragments under load experience relative motion, which determines the morphologic features of fracture repair. Perren proposed a hypothesis whereby the tissue response to the local mechanical factors influenced the repair process which he termed the "interfragmentary strain theory." This proposal related the tissue response to the local mechanical environment and integrated strain, sheer, and displacement with the physical events of fracture healing. In its simplest consideration, interfragmentary strain is defined by the movement of fracture ends relative to the initial gap width. Although the biological response of opposing bone and gap tissue has been defined with greater resolution with the advent of precise cell biology tools, the principles governing tissue formation and transformation following fracture still rely on sound clinical principles; fracture reduction; stable fixation; and adequate impetus to tissue regeneration. Bone regeneration occurs under tensile stress as achieved in tight apposition of adjacent bone surfaces with minimum shear force in movement. The implant 100 ("gasket component") compressed between the opposing two sections 11, 12 of the sternum 1 serve to reduce the micromotion at the adjoined surfaces to prevent interfragmentary strain. Other studies have shown that the axial loading and its effect on bone formation was considerably larger at the peripheral callus and in between osteotomy gaps but not in the intermedullary area. Larger peripheral callus and excess in tissue, for example bone tissue, at the level of the gap demonstrates more than three times larger mechanical rigidity for the axial than for the shear group ($p<0.05$). In summary, fixation that allows excessive shear movement significantly delays the healing of bone compared to healing under axial movement of the same magnitude.

Study Design

The implant 100 improves conventional sternal closure, and may enhance and/or accelerate post-operative recovery. Key indices of reduced post-operative pain, less analgesic use, improved breathing and chest wall mechanics, and improved early mobility with early hospital discharge are important clinical targets to sternal closure techniques. Mobility and functional recovery may be delayed after sternotomy due to the time required for osteosynthesis to be achieved through the normal healing process (6 to 8 weeks). It is widely believed that in the period before osteosynthesis occurs, sternal wires are placed under significant loading resulting in bone micromovement and substantial patient discomfort.

After the patients included in the study undergo sternotomy, the implant 100 can be used to stabilize the two halves of the separated sternum. Stabilization creates an environment that can promote bone healing/growth for fusion of the two sections 11, 12 of the separated sternum 1.

Conclusion

In conclusion, the implants 100 described herein reduce or eliminate the deficiencies experienced with use of conventional methods, inter alfa, sternal dehiscence, infection, post-operative pain, and/or scar tissue formation, approaching the goal of a sternum completely healed by new bone growth in the absence of complications.

The disclosures shown and described above are only examples. Even though numerous characteristics and advantages of the present technology have been set forth in the foregoing description, together with details of the structure and function of the present disclosure, the disclosure is illustrative only, and changes may be made in the detail, especially in matters of shape, size and arrangement of the parts within the principles of the present disclosure to the full extent indicated by the broad general meaning of the terms used in the attached claims. It will therefore be appreciated that the embodiments described above may be modified within the scope of the appended claims.

What is claimed is:

1. An implant operable to be disposed between and fuse two sections of a bone, the implant comprising:
   an inner layer;
   an outer layer at least partially surrounding the inner layer and operable to abut against the two sections of the bone, the outer layer being porous and/or fibrous and operable to receive at least one cellular growth factor; and
   a series of extension portions of the inner layer formed through the outer layer on at least one side of the outer layer, the extension portions spaced equidistant from each other along the outer layer, the extension portions operable to couple with the bone via a press-fit engagement.

2. The implant of claim 1,
   wherein,
   the outer layer includes a first portion and a second portion,
   the inner layer is sandwiched between the first and second portions of the outer layer.

3. The implant of claim 1, wherein the outer layer is wrapped around a circumference of the inner layer.

4. The implant of claim 1, wherein the inner layer and/or the outer layer includes at least a portion of at least one of cortical bone fibers, cancellous bone fibers, collagen sponge, cortical bone graft, synthetic bone, and/or tissue graft.

5. The implant of claim 1, wherein the at least one cellular growth factor includes bone morphogenetic proteins, mesenchymal stem cells, blood, osteoclasts, osteoblasts, antibiotics, analgesics, and/or medications.

6. The implant of claim 1, wherein the inner layer is fenestrated to promote bony ingrowth.

7. The implant of claim 1, wherein the implant has a thickness between about 2 millimeters and about 100 millimeters.

8. The implant of claim 1, wherein the implant has a length between about 25 millimeters and about 250 millimeters.

9. The implant of claim 1, wherein the implant has a depth between about 1 millimeter and about 30 millimeters.

10. The implant of claim 1, wherein the extension portions are teeth extending from the inner layer and through the outer layer, and operable to couple with the bone.

11. The implant of claim 10, wherein the teeth are formed of bone tissue, vicryl, polypropylene, stainless steel, titanium, polyether ether ketone (PEEK), polyetherketone (PEK), polymers, metals, and/or poly(methyl methacrylate) (PMMA).

12. The implant of claim 1, wherein the inner layer includes two tabs which extend from each end of the outer layer, the two tabs operable to provide compression and stability to assist in anchoring the implant between the two sections of the bone.

13. A method to fuse two sections of a bone, the method comprising:
   disposing an implant between the two sections of the bone, the implant including:
      an inner layer,
      an outer layer at least partially surrounding the inner layer and operable to abut against the two sections of the bone, the outer layer being porous and/or fibrous and operable to receive at least one cellular growth factor, and
      a series of extension portions of the inner layer formed through the outer layer on at least one side of the outer layer, the extension portions spaced equidistant from each other along the outer layer;
   compressing the implant between the two sections of the bone such that the outer layer is abutting against the two sections of the bone and the extension portions engage the bone via a press-fit engagement; and
   securing the compression of the implant and the two sections of the bone.

14. The method of claim 13, wherein the compression of the implant and the two sections of the bone is secured by wire.

15. The method of claim 13, wherein the inner layer and/or the outer layer includes at least a portion of at least one of cortical bone fibers, cancellous bone fibers, collagen sponge, cortical bone graft, synthetic bone, and/or tissue graft.

16. The method of claim 13, further comprising:
   soaking the implant in the at least one cellular growth factor,
   wherein the at least one cellular growth factor includes bone morphogenetic proteins, mesenchymal stem cells, blood, osteoclasts, osteoblasts, antibiotics, analgesics, and/or medications.

17. The method of claim 13, wherein the implant has a thickness between about 2 millimeters and about 100 millimeters.

18. The method of claim 13, further comprising:
   cutting the implant to a predetermined thickness, length, and/or depth.

19. The method of claim 13, wherein the extension portions are teeth extending from the inner layer, through the outer layer, and into the bone.

20. The method of claim 13, wherein the extension portions are formed of bone tissue, vicryl, polypropylene, stainless steel, titanium, polyether ether ketone (PEEK), polyetherketone (PEK), polymers, metals, and/or poly(methyl methacrylate) (PMMA).

* * * * *